United States Patent
Diolaiti

(10) Patent No.: US 9,629,520 B2
(45) Date of Patent: Apr. 25, 2017

(54) METHOD AND SYSTEM FOR MOVING AN ARTICULATED INSTRUMENT BACK TOWARDS AN ENTRY GUIDE WHILE AUTOMATICALLY RECONFIGURING THE ARTICULATED INSTRUMENT FOR RETRACTION INTO THE ENTRY GUIDE

(71) Applicant: Intuitive Surgical Operations, Inc., Sunnyvale, CA (US)

(72) Inventor: Nicola Diolaiti, Menlo Park, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 98 days.

(21) Appl. No.: 14/833,333

(22) Filed: Aug. 24, 2015

(65) Prior Publication Data
US 2016/0045272 A1   Feb. 18, 2016

Related U.S. Application Data

(63) Continuation of application No. 13/294,403, filed on Nov. 11, 2011, now Pat. No. 9,138,129, which is a
(Continued)

(51) Int. Cl.
*A61B 1/00* (2006.01)
*A61B 5/151* (2006.01)
(Continued)

(52) U.S. Cl.
CPC ...... *A61B 1/00163* (2013.01); *A61B 1/00087* (2013.01); *A61B 1/018* (2013.01);
(Continued)

(58) Field of Classification Search
CPC ..... A61B 1/00163; A61B 34/30; A61B 34/37; A61B 34/71; A61B 34/72; A61B 1/00087; A61B 1/018; A61B 5/15196
See application file for complete search history.

(56) References Cited

U.S. PATENT DOCUMENTS

| | | | |
|---|---|---|---|
| 3,628,535 A | 12/1971 | Ostrowsky et al. | |
| 3,818,284 A | 6/1974 | deVersterre et al. | |

(Continued)

FOREIGN PATENT DOCUMENTS

| | | |
|---|---|---|
| CN | 101160104 A | 4/2008 |
| EP | 514584 A2 | 11/1992 |

(Continued)

OTHER PUBLICATIONS

3D Slicer web site,http//www.slicer.org,2003.
(Continued)

*Primary Examiner* — Thomas G Black
*Assistant Examiner* — Sze-Hon Kong

(57) ABSTRACT

A medical robotic system includes articulated instruments extending out of a distal end of an entry guide. Prior to pivoting the entry guide to re-orient it and the instruments, the instruments are moved in tandem back towards the entry guide. Haptic cues and velocity limits are provided to assist the operator in the retraction of the instruments. After retraction, the entry guide may then be pivoted without concern that the instruments will harm patient anatomy. The movement of the instruments in tandem back towards the entry guide may also occur through coupled control modes while the entry guide is held in a fixed position and orientation.

10 Claims, 18 Drawing Sheets

Related U.S. Application Data continuation-in-part of application No. 12/780,071, filed on May 14, 2010, now Pat. No. 8,620,473, which is a continuation-in-part of application No. 11/762,200, filed on Jun. 13, 2007, now Pat. No. 7,725,214, application No. 14/833,333, which is a continuation-in-part of application No. 12/489,566, filed on Jun. 23, 2009, now Pat. No. 9,089,256, and a continuation-in-part of application No. 12/613,328, filed on Nov. 5, 2009, now Pat. No. 9,084,623, which is a continuation-in-part of application No. 12/541,913, filed on Aug. 15, 2009, now Pat. No. 8,903,546.

(51) Int. Cl.
*A61B 1/018* (2006.01)
*A61B 34/00* (2016.01)
*A61B 34/37* (2016.01)
*A61B 1/005* (2006.01)
*A61B 17/00* (2006.01)
*A61B 17/34* (2006.01)
*A61B 34/20* (2016.01)
*A61B 34/30* (2016.01)
*A61B 90/00* (2016.01)

(52) U.S. Cl.
CPC .......... *A61B 5/15196* (2013.01); *A61B 34/30* (2016.02); *A61B 34/37* (2016.02); *A61B 34/71* (2016.02); *A61B 34/72* (2016.02); *A61B 1/0055* (2013.01); *A61B 1/00193* (2013.01); *A61B 34/20* (2016.02); *A61B 90/361* (2016.02); *A61B 2017/00278* (2013.01); *A61B 2017/00694* (2013.01); *A61B 2017/3447* (2013.01); *A61B 2034/2061* (2016.02); *A61B 2034/301* (2016.02); *A61B 2034/305* (2016.02); *A61B 2034/306* (2016.02); *A61B 2090/062* (2016.02)

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,722,056 A | 1/1988 | Roberts et al. |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | LaBiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A | 2/1997 | Miyagi |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |

(56) References Cited

U.S. PATENT DOCUMENTS

| | | |
|---|---|---|
| 5,820,623 A | 10/1998 | Ng |
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster et al. |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1 | 1/2002 | Callahan |
| 6,358,749 B1 | 3/2002 | Orthman |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,436,107 B1 | 8/2002 | Wang et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Gerbi et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,659,939 B2 | 12/2003 | Moll et al. |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,714,839 B2 | 3/2004 | Salisbury et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,876,891 B1 | 4/2005 | Schuler et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,302,288 B1 | 11/2007 | Schellenberg |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 7,998,058 B2 | 8/2011 | Kura et al. |
| 8,005,571 B2 | 8/2011 | Sutherland et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,554,368 B2 | 10/2013 | Fielding et al. |
| 8,620,473 B2 | 12/2013 | Diolaiti et al. |
| 8,864,652 B2 | 10/2014 | Diolaiti et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,333,042 B2 | 5/2016 | Diolaiti et al. |
| 9,345,387 B2 | 5/2016 | Larkin |
| 9,469,034 B2 | 10/2016 | Diolaiti et al. |
| 9,492,927 B2 | 11/2016 | Diolaiti et al. |

(56) References Cited

U.S. PATENT DOCUMENTS

| | | |
|---|---|---|
| 9,516,996 B2 | 12/2016 | Diolaiti et al. |
| 2001/0035871 A1 | 11/2001 | Bieger et al. |
| 2002/0044104 A1 | 4/2002 | Friedrich et al. |
| 2002/0045905 A1 | 4/2002 | Gerbi et al. |
| 2002/0089544 A1 | 7/2002 | Jahn et al. |
| 2002/0120188 A1 | 8/2002 | Brock et al. |
| 2002/0156345 A1 | 10/2002 | Eppler et al. |
| 2002/0193800 A1 | 12/2002 | Kienzle, III et al. |
| 2003/0023347 A1 | 1/2003 | Konno et al. |
| 2003/0032878 A1 | 2/2003 | Shahidi |
| 2003/0055410 A1 | 3/2003 | Evans et al. |
| 2003/0060927 A1 | 3/2003 | Gerbi et al. |
| 2003/0109780 A1 | 6/2003 | Coste-Maniere et al. |
| 2003/0114730 A1 | 6/2003 | Hale et al. |
| 2003/0167103 A1 | 9/2003 | Tang et al. |
| 2003/0225479 A1 | 12/2003 | Waled |
| 2004/0024311 A1 | 2/2004 | Quaid |
| 2004/0034283 A1 | 2/2004 | Quaid, III |
| 2004/0039485 A1 | 2/2004 | Niemeyer et al. |
| 2004/0046711 A1 | 3/2004 | Triebfuerst |
| 2004/0077940 A1 | 4/2004 | Kienzle et al. |
| 2004/0106916 A1 | 6/2004 | Quaid et al. |
| 2004/0189675 A1 | 9/2004 | Pretlove et al. |
| 2004/0225183 A1 | 11/2004 | Michlitsch et al. |
| 2004/0238732 A1 | 12/2004 | State et al. |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1 | 1/2005 | Launay et al. |
| 2005/0054895 A1 | 3/2005 | Hoeg et al. |
| 2005/0059960 A1 | 3/2005 | Simaan et al. |
| 2005/0096502 A1 | 5/2005 | Khalili |
| 2005/0113640 A1 | 5/2005 | Saadat et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2006/0058988 A1 | 3/2006 | Defranoux et al. |
| 2006/0142657 A1 | 6/2006 | Quaid et al. |
| 2006/0149129 A1 | 7/2006 | Watts et al. |
| 2006/0161045 A1 | 7/2006 | Merril et al. |
| 2006/0178559 A1 | 8/2006 | Kumar et al. |
| 2006/0258938 A1 | 11/2006 | Hoffman et al. |
| 2006/0261770 A1 | 11/2006 | Kishi et al. |
| 2007/0013336 A1 | 1/2007 | Nowlin et al. |
| 2007/0016174 A1 | 1/2007 | Millman et al. |
| 2007/0021738 A1 | 1/2007 | Hasser et al. |
| 2007/0032906 A1 | 2/2007 | Sutherland et al. |
| 2007/0038080 A1 | 2/2007 | Salisbury, Jr. et al. |
| 2007/0060879 A1 | 3/2007 | Weitzner et al. |
| 2007/0081714 A1 | 4/2007 | Wallack et al. |
| 2007/0106307 A1 | 5/2007 | Bodduluri et al. |
| 2007/0135803 A1 | 6/2007 | Belson |
| 2007/0138992 A1 | 6/2007 | Prisco et al. |
| 2007/0142968 A1 | 6/2007 | Prisco et al. |
| 2007/0144298 A1 | 6/2007 | Miller |
| 2007/0177009 A1 | 8/2007 | Bayer et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2007/0296366 A1 | 12/2007 | Quaid et al. |
| 2008/0004603 A1 | 1/2008 | Larkin et al. |
| 2008/0033240 A1 | 2/2008 | Hoffman et al. |
| 2008/0065099 A1 | 3/2008 | Cooper et al. |
| 2008/0065105 A1 | 3/2008 | Larkin et al. |
| 2008/0065109 A1 | 3/2008 | Larkin |
| 2008/0071291 A1 | 3/2008 | Duval et al. |
| 2008/0081992 A1 | 4/2008 | Kagermeier |
| 2008/0118115 A1 | 5/2008 | Williamson |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326322 A1 | 12/2009 | Diolaiti |
| 2009/0326552 A1 | 12/2009 | Diolaiti |
| 2009/0326553 A1 | 12/2009 | Mustufa et al. |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0317965 A1 | 12/2010 | Itkowitz et al. |
| 2010/0331855 A1 | 12/2010 | Zhao et al. |
| 2010/0331856 A1 | 12/2010 | Carlson et al. |
| 2011/0071675 A1 | 3/2011 | Wells et al. |
| 2011/0105898 A1 | 5/2011 | Guthart et al. |
| 2011/0196199 A1 | 8/2011 | Donhowe et al. |
| 2011/0290856 A1 | 12/2011 | Shelton, IV et al. |
| 2011/0313573 A1 | 12/2011 | Schreiber et al. |
| 2012/0059391 A1 | 3/2012 | Diolaiti et al. |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0231680 A1 | 9/2013 | Diolaiti et al. |
| 2013/0245375 A1 | 9/2013 | Dimaio et al. |
| 2013/0289767 A1 | 10/2013 | Lim et al. |
| 2014/0052150 A1 | 2/2014 | Taylor et al. |
| 2014/0055489 A1 | 2/2014 | Itkowitz et al. |
| 2014/0135792 A1 | 5/2014 | Larkin et al. |
| 2014/0222021 A1 | 8/2014 | Diolaiti et al. |
| 2014/0232824 A1 | 8/2014 | Dimaio et al. |
| 2015/0065793 A1 | 3/2015 | Diolaiti et al. |
| 2015/0150639 A1 | 6/2015 | Diolaiti et al. |
| 2015/0182287 A1 | 7/2015 | Guthart et al. |
| 2015/0297300 A1 | 10/2015 | Gomez et al. |
| 2015/0366625 A1 | 12/2015 | Tognaccini et al. |
| 2016/0235486 A1 | 8/2016 | Larkin |
| 2016/0242860 A1 | 8/2016 | Diolaiti et al. |

FOREIGN PATENT DOCUMENTS

| | | |
|---|---|---|
| EP | 0646358 A1 | 4/1995 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| JP | S61230895 A | 10/1986 |
| JP | H01280449 A | 11/1989 |
| JP | H04231034 A | 8/1992 |
| JP | H07184923 A | 7/1995 |
| JP | H07265321 A | 10/1995 |
| JP | H0889506 A | 4/1996 |
| JP | H08107875 A | 4/1996 |
| JP | H08154321 A | 6/1996 |
| JP | H08215211 A | 8/1996 |
| JP | H08275958 A | 10/1996 |
| JP | H08299363 A | 11/1996 |
| JP | H09141580 A | 6/1997 |
| JP | H10146341 A | 6/1998 |
| JP | H11309 A | 1/1999 |
| JP | 2000500679 A | 1/2000 |
| JP | 2000300579 A | 10/2000 |
| JP | 2001000448 A | 1/2001 |

(56) References Cited

FOREIGN PATENT DOCUMENTS

| | | |
|---|---|---|
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005303327 A | 10/2005 |
| JP | 2005334650 A | 12/2005 |
| JP | 2007029232 A | 2/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009039814 A | 2/2009 |
| JP | 2009525097 A | 7/2009 |
| JP | 2009537229 A | 10/2009 |
| WO | WO-9501757 A1 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-03061482 A1 | 7/2003 |
| WO | WO-2004014244 A2 | 2/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008103383 A1 | 8/2008 |
| WO | WO-2009034477 A2 | 3/2009 |
| WO | WO-2009037576 A2 | 3/2009 |
| WO | WO-2009044287 A2 | 4/2009 |
| WO | WO-2009158164 A1 | 12/2009 |
| WO | WO-2010039394 A1 | 4/2010 |

OTHER PUBLICATIONS

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18-Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew, Scott R. et al., "Ground control testbed for space station freedom robot manipulators," IEEE Virtual Reality Annual International Symposium, 1993, pp. 69-75, IEEE.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total, Morgan kaufmann publishers, Inc.

Bartels, Richard H. et al., "Solution of the Matrix Equation AX+XB=C," Communications of the ACM, 1972, pp. 820-826, vol. 15-Issue 9, ACM Press.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K. et al., "Controlling Remote Manipulators through Kinesthetic Coupling," Computers in Mechanical Engineering, 1983, pp. 48-60, vol. 1-Issue 1.

Ben Gayed, M. et al., "An Advanced Control Micromanipulator for Surgical Applications," Systems Science, 1987, pp. 123-134, vol. 13.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-921, vol. 19-Issue 5, IEEE.

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Sicence, 2001, pp. 1426-1429, vol. 2208.

Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.

Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Bettini, Alessandro et al., "Vision Assisted Control for Manipulation Using Virtual Fixtures," IEEE Transactions on Robotics, 2004, pp. 953-966, vol. 20—Issue 6, IEEE.

Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.

Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.

Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.

Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.

(56) References Cited

OTHER PUBLICATIONS

Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the Internationa Conference on Computational Science-Part II, Lecture Notes in Computer Science , 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burdea, Grigore et al., "Dextrous Telerobotics with Force Feedback—an overview. Part 2: Control and Implementation," Robotica, 1991, pp. 291-298, vol. 9.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52-Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes In Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.
Bzostek, Andrew, "Image Guided Percutaneous Pattern Placement in Souft Tissue," The Johns Hopkins University Dept. of Computer Science: Baltimore, 1997, pp. 2007-01-2007-22.
Cadeddu, Jeffrey A. et al., "A Robotic System for Percutaneous Renal Access," The Journal of Urology, 1997, pp. 1589-1593, vol. 158-Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.
Carr, J., "Surface reconstruction in 3D medical imaging," PhD Thesis, University of Canterbury, Christchurch, New Zealand, 1996, 223 Pages.
Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.
Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.
Chinzei, Kiyoyuki et al., "MR Compatible Surgical Assist Robot: System Integration and Preliminary Feasibility Study," in Proceedings of Third International Conference On Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6-issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Christensen, B. et al., "Model based sensor directed remediation of underground storage tanks," International Conf. on Robotics and Automation, Sacramento, CA, Apr. 1991, pp. 1377-1383, vol. 2. IEEE.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the Art in Surgical Robotics:Clinical Applications and Technology Challenges," Computer Aided Surgery, 2001 [retrieved on Feb. 24, 2002], pp. 1-26.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
D'Angelica M., "Staging Laparoscopy for Potentially Respectable Noncolorectal," Ann Surg Oncol, 2002, pp. 204-209, vol. 9—No. 2, Lippincott Williams & Wilkins.

(56) References Cited

OTHER PUBLICATIONS

Daniilidis, Konstantinos, Hand-Eye Calibration Using Dual Quaternions, Int. J. of Robotics Research, 2000, pp. 286-298, vol. 19—No. 3, Sage Publications, Inc.

Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.

Davies, S. C.et al., "Ultrasound quantitaion of respiratory organ motion in the upper abdomen," British Journal of Radiology, 1994, pp. 1096-1102, vol. 37—Iss. 803.

De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.

Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.

DeGoulange, E. et al., "HIPPOCRATE: an intrinsically safe robot for medical applications," IEEE/RSH International Conference on Intelligent Biomedicine, 1998, pp. 959-964, vol. 2, IEEE.

DelGorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.

DeWan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 2, Springer-Verlag.

Dodds, Zachary et al., "A hierarchical architecture for vision-based robotic manipulation tasks," in Proceedings of the International Conference on Vision Systems, 1999, pp. 312-330, vol. 542, Springer-Verlag.

Doggett, Stephen, W., "Image Registered Real Time Intra-Operative Treatment Planning: Permanent Seed Brachytherapy," 2000, pp. 4.

Dolan, J.M. et al., "A Robot in an Operating Room: A Bull in a China Shop," 1987, pp. 1096-1097, vol. 2.

Elder, Matthew C. et al., "Specifying user interfaces for safety critical medical systems," Second Annual International Symposium on Medical Robotics and Computer Assisted Surgery, Nov. 1995, pp. 148-155.

Eldridge, B. et al., "A Remote Center of Motion Robotic Arm for Computer Assisted Surgery," Robotica, 1996, pp. 103-109, vol. 14 Issue 1.

Ellsmere, James et al., "A navigation system for augmenting laparoscopic ultrasound," Medical Image Computing and Computer-Assisted Intervention, Lecture Notes in Computer Science, 2003, pp. 184-191, Springer.

Extended European Search Report for Application No. 12848026.6 mailed on Jul. 29, 2015, 8 pages.

Fattal, Lischinsk, "Variational Classification for Visualization of 3D Ultrasound Data," Proceedings of the conference on Visualization, 2001, pp. 403-410, IEEE Computer Society.

Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.

Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.

Fichtinger, Gabor et al., "Robotically Assisted Percutaneous Local Therapy and Biopsy," 10th International Conference of Advance Robotics, 2001, pp. 133-151, IEEE.

Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.

Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.

Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.

Fisher, Scott S., "Virtual interface environment," IEEE/A1AA 7th Digital Avionics Systems Conference Ft. Worth Texas, 1986, pp. 346-350, IEEE.

Frantz D.D et al., "Accuracy assessment protocols for electromagnetic tracking systems," Physics in Medicine and Biology, 2003, pp. 2241-2251, Issue 48.

Fu, K.S. et al., "Robotics: control, sensing, vision, and intelligence," 1987, pp. 12-76 and 201-265, Ch. 2 & 5, McGraw-Hill Book Company.

Fuchs, Henry et al., "Augmented Reality Visualization for Laparoscopic Surgery," Medical Image Computing and Computer-Assisted Intervention, 1998, pp. 934-943, vol. 1496, Springer-Verlag.

Fukuda, Toshio et al., "A new method of master-slave type of teleoperation for a micro-manipulator system," IEEE Microrobots and Teleoperations Workshop, 1987, 5 pages, IEEE.

Funda, Janez, "An experimental user interface for an interactive surgical robot," In 1st International Symposium on Medical Robotics and Computer Assisted Surgery (MRCAS 94), Pittsburgh, 1994, pp. 196-201, 203.

Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Funda, Janez et al., "Control and evaluation of a 7-axis surgical robot for laparoscopy," IEEE Int. Conf. on Robotics and Automation, 1995, pp. 1477-1484, vol. 2, IEEE.

Funda, Janez et al., "Image-Guided Command and Control of a Surgical Robot," Proc. Medicine Meets Virtual Reality II, 1994, pp. 52-57.

Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.

Furuta, Katsuhisa et al., "Master slave manipulator based on virtual internal model following control concept," IEEE Intl. Conference on Robotics and Automation, 1987, pp. 567-572, vol. 1, IEEE.

Ganssle J.G.,,A Guide to Debouncing,The Ganssle Group,Jun. 2008,26 pages.

Garrett, William F. et al., "Real-Time Incremental Visualization of Dynamic Ultrasound Volumes Using Parallel BSP Trees," IEEE Proceedings Visualization, 1996, pp. 235-240, 490, IEEE.

Gee, Andrew et al., "Processing and visualizing three-dimensional ultrasound data," Journal of Radiology, 2004, pp. 186-193, vol. 77.

Gelb, Arthur et al., "Applied Optimal Estimation," 1974, 4 Pages Total.

Gennari, G. et al., "Probabilistic data association methods in visual tracking of groups," IEEE Conference on Computer Vision and Pattern Recognition, 2004, pp. 1-790-1-797, vol. 1—issue. 27, IEEE.

Gigot, Jean-Francois et al., "Laparoscopic Liver Resection for Malignant Liver Tumors Prclimary Results of a Multicenter European Study," Ann Surg, 2002, pp. 90-97, vol. 236—issue 1.

Gonzales, Adriana Vilchis et al., "A system for Robotic Tele-echography," Medical Image Computing and Computer-Assisted Intervention, 2001, pp. 326-334, vol. 2208, Springer.

Green, Philip, S. et al., "Mobile telepresence surgery," 2nd Annual Intl Symposium on Med. Robotics and Computer Assisted Surgery, Maryland Nov. 1995, pp. 97-103.

Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.

(56) References Cited

OTHER PUBLICATIONS

Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.

Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.

Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.

Hager Gregory D. et al., "Multiple Kernel Tracking with SSD," Proceedings of the IEEE Conference on Computer Vision and Pattern Recognition (CVPR 2004), 2004, pp. 1-790-1-797, vol. 1—issue 27, IEEE.

Hager, Gregory D. et al., "The XVision System: A Portable Substrate for Real Time Vision Applications," 1998, pp. 23-37, vol. 69—issue 1.

Hannaford, Blake et al., "Experimental and simulation studies of hard contact in force reflecting teleoperation," IEEE International Conference on Robotics and Automation Proceedings, 1988, pp. 584-589, vol. 1, IEEE.

Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.

Harris, S.J. et al., "A robotic procedure for transurethral resection of the prostate," Second Annual International Symposium on Medical Robotics and Computer Assisted Surgery, 1995, pp. 264-271.

Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.

Herline, Alan J. et al., "Image-Guided Surgery: Preliminary Feasibility Studies of Frameless Stereotactic Liver Surgery," Archives of Surgery, 1999, pp. 644-650, vol. 134—No. 6.

Herline, Alan J. et al., "Surface Registration for Use in Interactive," Image-Guided Liver Surgery, Computer Aided Surgery, 2000, pp. 11-17, vol. 5—No. 2.

Herman, Barry C., et al, "Telerobotic surgery creates opportunity for augmented reality surgery," Abstract No. T1F2, Telemedicine Journal and E-Health, vol. 11, Issue 2, p. 203, Apr. 2005.

Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.

Hespanha J.P. et al., "What Tasks Can Be Performed with an Uncalibrated Stereo Vision System", International Journal of Computer Vision, 1999, pp. 65-85, vol. 35—issue. (1).

Hill, John W., "Telepresence surgery demonstration system," Robotics and Automation, 1994, pp. 2302-2307, vol. 3, SRI International.

Ho, S. C.et al., "Robot Assisted Knee Surgery," IEEE Engineering in Medicine and Biology Magazine, 1995, pp. 292-300, vol. 14—Iss. 3, IEEE.

Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.

Horn, Berthold K.P., "Closed-form solution of absolute orientation using unit quaternions," Journal of the Optical Society of America A, vol. 4, No. 4, pp. 629-642, Apr. 1987.

Hunter, Ian W. et al., "A teleoperated microsurgical robot and associated virtual environment For eye surgery," Presence: Teleoperators and Virtual Environments, 1993, pp. 265-280, vol. 2—No. 4, MIT Press.

Hunter, Ian W. et al., "Ophthalmic microsurgical robot and associated virtual environment," Comput. Biol. Med, 1995, vol. 25, Issue 2, pp. 173-182, Pergamon.

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.

Hutchinson, Seth et al., "A Tutorial Visual Servo Control," IEEE Transactions on Robotics and Automation, 1996, pp. 651-670, vol. 12 issue.5, IEEE.

IEEE Systems and Software Engineering—Recommended Practice for Architectural Description of Software-Intensive Systems, IEEE Std 1471-2000, 34 pages, First Edition, Jul. 15, 2007.

Inoue, Masao; "Six-Axis bilateral control of an articulated slave manipulator using a Cartesian master manipulator," Advanced robotics, 1990, pp. 139-150, vol. 4—Issue 2, Robotic society of Japan.

International Preliminary Examination Report for Application No. PCT/US00/08526, mailed on Jun. 29, 2001, 4 pages.

International Search Report and Written Opinion for Application No. PCT/US2012/064379, mailed on Mar. 29, 2013, 12 pages.

Intuitive Surgical, Inc., "Intuitive Surgical daVinci API v5.0 Reference Manual," generated Jul. 17, 2006, 149 pages.

Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.

Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.

Johns Hopkins University and Intuitive Surgical, Inc., "System Requirements for the Surgical Assistant Workstation," Rev. 2, Jan. 29, 2007, 17 pages.

Jones, Daniel B. et al., "Next generation 3D videosystems may improve laprascopic task performance," Interactive Technology and the New Paradigm for Healthcare, 1995, pp. 152-160, Ch 25.

Joskowicz, Leo et al., "Computers in Imaging and Guided Surgery," Computing in Science and Engineering, 2001, pp. 65-72, vol. 3—Issue: 5, IEEE.

Jurie, Frederic et al., "Hyperplane Approximation for Template Matching," IEEE Transactions on Pattern Analysis and Machine Intelligence (PAMI), 2002, pp. 996-1000, vol. 24—Issue 7, IEEE.

Kane, Robert A., "Intraoperative Ultrasonography, History, Current State of the Art, and Future Directions," J Ultrasound Med, 2004, pp. 1407-1420, vol. 23.

Kaplan, Irving, "Minimizing Rectal and Urinary Complications in Prostate Brachytherapy," Journal of Endourology, 2000, pp. 381-383.

Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.

Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.

Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI,, Lecture Notes in Computer Science, 2003, vol. 1, Springer.

Kapoor, Ankur et al., "Suturing in Confined Spaces: Constrained Motion Control of a Hybrid 8-DOF Robot," Proceedings, 12th International Conference on Advanced Robotics, 2005, pp. 452-459.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

Kavoussi, Louis R., "Laparoscopic donor nephrectomy," Kidney International, 2000, pp. 2175-2186, vol. 57.

(56) References Cited

OTHER PUBLICATIONS

Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H., "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kilmer, R. D. et al., "Watchdog safety computer design and implementation," RI/SME Robots 8 Conference, Jun. 1984, pp. 101-117.
Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.
Kitagawa, Masaya et al., "Effect of Sensory Substitution on Suture Manipulation Forces for Surgical Teleoperation," 12th Annual Medicine Meets Virtual Reality Conference, 2005, 8 pages.
Koizumi, Naoshi et al., "Development of Three-Dimensional Endoscopic Ultrasound System with Optical Tracking," Medical Image Computing and Computer-Assisted Inteervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Kragic D. et al., "Human-Machine Collaborative Systems for Microsurgical Applications," International Symposium on Robotics Research, 2005, pp. 731-741, vol. 24—Issue 9, Sage Publication.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention-Part , Lecture Notes in Computer Science, 2002, pp. 9-16, vol. 2488, Springer Verlag.
Kumar, Rajesh, "An Augmented Steady Hand System for Precise Micromanipulation," 2001, 109 pages.
Kumar, Rajesh et al., "An Augmentation System for Fine Manipulation," Proceedings of the Third International Conference on Medical Image Computing and Computer-Assisted Intervention, Lecture Notes In Computer Science, 2000, pp. 956-964, vol. 1935, Springer Verlang.
Kumar, Rajesh et al., "Application of Task-Level Augmentation for Cooperative Fine Manipulation Tasks in Surgery," Proceedings of the 4th International Conference on Medical Image Computing and Computer-Assisted Interventions, Lecture Notes In Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
LacRoute, Phillippe et al., "The VolPack Volume Rendering Library," 2003, pp. 4.
LacRoute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surger, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.
Lavonius, Maija I. et al., "Staging of Gastric Cancer: A Study with Spiral Computed Tomography, Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.
Lawson, Charles L. et al., "Linear least squares with linear inequality constraints Solving Least Squares Problems," 1974, pp. 158-173, Prentice Hall Inc.
Lazarevic, Zoran, "Feasibility of a Stewart Platform with Fixed Actuators as a Platform for CABG Surgery Device," 1997, 45 pages, Master's Thesis Columbia University Department of Bioengineering.
Lee Jr, Fred T. et al., "CT-monitoried percutaneous cryoablation in a pig liver model," Radiology, 1999, pp. 687-692, vol. 211(3).
Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.
Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.
Levoy, Marc, "Display of Surfaces from Volume Data," IEEE Computer Graphics and Applications, 1988, pp. 29-37, vol. 8—Iss. 3, IEEE.
Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.
Li, Ming and Russell H. Taylor, "Performance of surgical robots with automatically generated spatial virtual fixtures," IEEE International Conference on Robotics and Automation, Barcelona, Spain, Apr. 2005, pp. 217-222.
Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

(56) References Cited

OTHER PUBLICATIONS

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, HAPTICS 2003, 11th Symposium on Haptic Interfaces for Virtual Environment and Teleoperator Systems, Mar. 22-23, 2003, pp. 125-131, IEEE.

Li, Ming, "Intelligent Robotic Surgical Assistance for Sinus Surgery," Ph.D. Dissertation, Computer Science, Johns Hopkins University, Baltimore, 2005, 229 pages.

Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer.

Loser, Michael H. et al., "Visual servoing for automatic and uncalibrated percutaneous procedures," SPIE Medical Imaging, 2000, pp. 270-281, vol. 3976, SPIE.

Madhani, Akhil J., "Design of Teleoperated Surgical Instruments for Minimally Invasive Surgery," Feb. 1998, pp. 1-251.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. By Lippincott Williams & Wilkins, Philadelphia, 2004, pp. 26-31.

Masamune K., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.

Mayer, Hermann et al., "Skill Transfer and Learning by Demonstration, in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: expereince of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

Mitsuishi, Mamoru et al., "A tele-micro-surgery system with co-located view and operation points and a rotational-force-feedback-free master manipulator," 2nd Annual Intl. Sumposium on Medical robotics and Computer Assisted Surgery Baltimore Maryland, Nov. 4-7, 1995, pp. 111-118.

Mitsuishi, Mamoru et al., "Remote Ultrasound Diagnostic System," Conf. on Robotics and Automation, 2001, pp. 1567-1574, vol. 2. IEEE.

Mourgues, Fabienet al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes In Computer Science, 2002, pp. 25-34, vol. 2488, Springer-Verlag.

Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.

Nakakura, Eric K et al., "Hepatocellular Carcinoma: Current Management Recommendations," Advances on Oncology, 2000, pp. 12-18, vol. 16—No. 2.

Neisius B. et al., "Robotic manipulator for endoscopic handling of surgical effectors and cameras," 1st Intl. Symposium on Medical Robotics and Computer Assisted Surgery, 1994, pp. 169-175, vol. 2.

Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.

Nelson, Thomas, R. et al., "Three-dimensional ultrasound imaging," Ultrasound in Medicine & Biology, 1998, pp. 1243-1270, vol. 24—No. 9, Elsevier.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue. 1, IEEE.

Novotny Paul M. et al., "Tool Localization in 3D Ultrasound Images," Medical Image Computing and Computer-Assisted Intervention, 2003, pp. 969-970, vol. 2879, Springer.

Office Action mailed May 1, 2012 for Japanese Application No. 20090518470 filed Jun. 22, 2007, 7 pages.

Office Action mailed Sep. 3, 2014 for Japanese Application No. JP20120503535 filed Mar. 26, 2010.

Office Action mailed Jan. 26, 2015 for Japanese Application No. 20130186992 filed Sep. 10, 2013, 9 pages.

Office Action mailed Jun. 12, 2015 for Japanese Application No. 20130186992 filed Sep. 10, 2013, 8 pages.

Ohbuchi, Ryutarou et al., "Incremental Volume Reconstruction and Rendering for 3D Ultrasound Imaging," The International Society of Optical Engineering, 1992, pp. 312-323, vol. 1808, SPIE.

(56) References Cited

OTHER PUBLICATIONS

Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.

Patriciu Alexandru et al., "Motion-based robotic instrument targeting under c-arm fluoroscopy," Medical Image Computing and Computer-Assisted Interventions, 2000, pp. 988-998, vol. 1935, Springer.

Paul, Howard A. et al., "Development of a Surgical Robot for Cementless Total Hip Arthroplasty," Clinical Orthopaedics, Dec. 1992, pp. 57-66, vol. 285.

Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.

Pose—definition from Merriam Webster Dictionary, 4 pages, [online], [retrieved on Apr. 3, 2015]. Retrieved from the Internet: URL: http://www.merriam-webster.com/dictonary/pose.

Posture—definition from Merriam Webster Dictionary, 4 pages, [online], [retrieved on Apr. 3, 2015]. Retrieved from the Internet: URL: http://www.merriam-webster.com/dictonary/posture.

Poulose P. K et al., "Human vs Robotic Organ Retraction During Laparoscopic Nissen Fundoplication," Surgical Endoscopy, 1999, pp. 461-465, vol. 13, Springer-Verlag.

Prager Richard et al., "Practical segmentation of 3D ultrasound," In Proceedings of Medical Image Understanding and Analysis, 1999, pp. 161-164.

Prager Richard et al., "Rapid Calibration for 3D Freehand Ultrasound," Ultrasound in Medicine and Biology, 1998, pp. 855-869, vol. 24—No. 6, Elsevier.

Prasad, Srinivas K. et al., "A minimally invasive approach to pelvic osteolysis," 2002, in Proc. Computer-Assisted Orthopaedic Surgery (CAOS), pp. 349-350.

Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.

Preising, B. et al., "A Literature Review: Robots in Medicine," IEEE Engineering in Medicine and Biology, 1991, pp. 13-22, 71, vol. 10—Issue 2, IEEE.

Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.

Ramey, Nicholas A., "Stereo-Based Direct Surface Tracking with Deformable Parametric Models," 2003, 104 Pages Total.

Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

Ratner, Lloyd E. et al, "Laparoscopic live donor nephrectomy removes disincentives to live donation," Transplantation, 1997, pp. 3402-3403, vol. 29—Issue 8, Elsevier.

Ratner, Lloyd E. et al., "Laparoscopic live donor nephrectomy," Transplantation, 1995, pp. 1047-1049.

Rau, Beate, M. eta al., "Is There Additional Information From Laparoscopic Ultrasound in Tumor Staging", Digestive Surgery, 2002, pp. 479-483, vol. 19—No. 6.

Rockall, Timothy A., "The da Vinci Telerobotic Surgical System," Chapter 8 in Primer of Robotic & Telerobotic Surgery, Eds. Garth H. Ballantyne et al., Pub. by Lippincott Williams & Wilkins, Philadelphia, 2004, pp. 57-60.

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Human interface hardware for virtual laparoscopic surgery," Proceedings of the Interactive Technology and the New Paradigm for Healthcare, 1995, pp. 322-325, Amsterdam: IOS Press.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Sastry, Shankar et al., "Millirobotics for remote minamally invasive surgery," Proceedings of the Intl. Workshop on Some Critical Issues in Robotics, Singapore, Oct. 2-3, 1995, pp. 81-98.

Sastry, Shankar, http://robotics.eecs.berkeley.edu, Nov. 1, 1995, Total 8 pages.

Sastry, Shankar, "MilliRobotics in Minimally Invasive Telesurgery," Internet, http://robotics.eecs.berkeley.edu, 1996, 8 pages.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Sicence, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radionfrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

(56) References Cited

OTHER PUBLICATIONS

Solomon, Stephen B. et al., "CT Guided Robotic Needle Biopsy: A Precise Sampling Method Minimizing Radiation Exposure to the Physician, Radiology," 2002, pp. 277-282, vol. 225.
Solomon, Stephen B. et al., "Robotically Driven Interventions: A Method of Using CT Fluoroscopy without Radiation Exposure to ther Physician," Radiology, 2002, pp. 277-282, vol. 225.
Solus—3D web site: Last updated Jun. 24, 1999; downloaded Jul. 5, 2007.
Sommer, Graham et al., "Liver tumors utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions om Medical Imaging, 2000, pp. 1012-1023, vol. 19—No. 10, IEEE.
Stetten, George D et al., "Overlayiing Ultrasound Images on Direct Vision," Journal of Ultrasound in Medicine, 2001, pp. 235-240, vol. 20—No. 3.
Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.
Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.
Stoianovici, Dan et al., "Robotic For Precise Percutaneous Needle Insertion," In Thirteenth Annual Meeting of the Society for Urology and Engineering. San Diego, May 1998, pp. 4.
Stoianovici, Dan et al., "Robotic Telemanipulation for Percutaneous Renal Access," 16th World Congress on Endourology, 1998, pp. S201.
Stoll, Jeff, "Ultrasound-based servoing of manipulators for telesurgery," Telemanipulator and Telepresence Technologies VIII Conference, 2001, pp. 78-85, SPIE.
Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.
Suramo, I. et al., "Cranio-caudal movements of the liver, pancreas and kidneys in respiration," Acta Radiologica: Diagnosis, 1984, pp. 129-131, vol. 25, Radiological Societies.
Susil, Robert, C. et al., "A Single Image Registration Method for CT Guided Interventions," 2nd International Symposium on Medical Image Computing and Computer-Assisted Interventions (MICCAI'99),Lecture Notes in Computer Sicence, 1999, pp. 798-808, vol. 1679, Srpinger-Verlag.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.
Taubes, Gary et al., "Surgery in Cyberspace," Discover magazine, Dec. 1994, vol. 15, issue 12, pp. 85-92.
Tavakoli, M., et al, A Force Reflective Master-Slave System for Minimally Invasive Surgery, Proc. IEEE/RSJ International Conference on Intelligent Robots and Systems, 2003, pp. 3077-3082, vol. 4, IEEE.
Taylor, Russell H., "A Perspective on Medical Robotics," Proceedings of the IEEE, vol. 94, No. 9, Sep. 2006, pp. 1652-1664.

Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. and Christopher Hasser, "Development of a Surgical Assistant Workstation for Teleoperated Surgical Robots," NSF Proposal No. 0646678, Aug. 2006, 16 pages.
Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.
Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.
Taylor, Russell H. et al., "A Computational Architecture for Programmable Automation Research," Conference on Intelligent Robots and Computer Vision, 1986, pp. 438-440, vol. 726, SPIE.
Taylor, Russell H. et al., "A General Purpose Control Architecture for Programmable Automation Research," Proceedings of the Third International Symposium on Robotics, 1986, pp. 165-174, MIT Press.
Taylor, Russell, H et al., "A Steady-Hand Robotic System for Microsurgical Augmentation," International Journal of Robotics Research, 1999, pp. 1201-1210, vol. 18—No. 12, Springer-Verlag.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "A Telerobotic System for Augmentation of Endoscopic Surgery," In IEEE Conference on Engineering in Medicine and Biology, vol. 14, 1992, pp. 1054-1056, vol. 3, IEEE.
Taylor, Russell, H et al., "AML a Manufacturing Language," The International Journal of Robotics Research, 1982, pp. 19-41, vol. 1—No. 3, SAGE Publications.
Taylor, Russell H. et al., "An Image-directed Robotic System for Hip Replacement Surgery," J. Robotics Society of Japan, 1990, pp. 615-620, vol. 8—issue 5.
Taylor, Russell, H. et al., "An Integrated Robot Systems Architecture," Proceedings of the IEEE, 1983, pp. 842-856, vol. 71—Issue 7, IEEE.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Computer-Integrated Surgery," 1996, 8 Pages, MIT Press.
Taylor, Russell H. et al., "Medical Robotics and Computer-Integrated Surgery," Chapter 52 in Springer Handbook of Robotics, Springer, 2008, pp. 1199-1222.
Taylor, Russell H. et al., "Medical Robotics in Computer-Integrated Surgery," IEEE Transactions on Robotics and Automation, 2003, pp. 765-781, vol. 19—No. 5, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.
Taylor, Russell, H et al., "The Architecture of an Integrated Robot System," First Int. Conf. on Advanced Robotics (ICAR)., 1983, pp. 389-398.
Taylor, Russell H. "Medical Robotics and Computer-Integrated Surgery," Handbook of Industrial Robotics, Second Edition, 1999, pp. 1213-1230, Chapter 65, John Wiley & Sons.
Taylor, Russell H. "Medical Robots," in Computer and Robotic Assisted Knee and Hip Surgery, 2004, pp. 54-59, Oxford Press.

(56) References Cited

OTHER PUBLICATIONS

Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.
Taylor, Russell H. "The Planning and Execution of Straight Line Manipulator Trajectories," IBM Journal of Research and Development, 1979, pp. 424-436, vol. 23—Issue 4.
Taylor, Russell H., "Ultrasound Assistant for a Laparoscopic Surgical Robot," NIH STTR Phase II Proposal R42-RR019159, revised May 2001, 54 pages.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572, vol. 60—No. 4, Elsevier.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Toon, John, "Virtual Reality for Eye Surgery," Georgia Tech Research News, 1993, 4 Pages.
Toyama, Kentaro et al., "Incremental Focus of Attention for Robust Visual Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robits and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Uecker, Darrin R. et al., "A Speech-Directed Multi-Modal Man-Machine Interface for Robotically Enhanced Surgery," 1994, pp. 176-183.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
U.S. Appl. No. 11/583,963 Non-Final Office Action mailed Jul. 9, 2009, 40 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master Slave Robots," Motor-con, 1987, pp. 309-316.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster Robert J. et al., "Design Considerations for Robotic Needle Steering," International Conference on Robotics and Automation, 2005, pp. 3588-3594, IEEE.
Webster Robert J. et al "Nonholonomic Modeling of Needle Steering," The International Journal of Robotics Research, 2004, pp. 509-525, vol. 25—No. 5-6, SAGE Publications.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Wei, Zhouping et al "Robot-assisted 3D-TRUS guided prostate brachytherapy: system integration and validation," Medical Physics, 2004, pp. 539-548, vol. 31—No. 3.
Wengert, Christian, "Camera Calibration Toolbox for Matlab," [online][retrieved on Oct. 24, 2006], Retrieved from the Internet: <url:>, 5 pages.<url:></url:</url:>.
Wilhelm, Dirk et al., "Electromagnetically Navigated Laparoscopic Ultrasound," Surg. Technol. Int, 2003, pp. 50-54, vol. 11.
Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.
Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.
Xu, Sheng et al., "3D Motion Tracking of Pulmonary Lesions Using CT Fluoroscopy Images for Robotically Assisted Lung Biopsy," International Society of Optical Engineering, 2004, pp. 394-402, SPIE.
Yamagata, Hitoshi, "Development of a New Display Method for Compound 3D Ultrasound Images: Fusion 3D Images From B-mode and 3D Doppler Images," 1999, pp. 43-46, vol. 70.
Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.
Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.
Yao, Jianhua et al., "Deformable registration between a statistical born density atlas and X-ray images," Second International Conference on Computer Assisted Orthopaedic Surgery, 2002, pp. 168-169.
Zacherl, Johannes et al., "Current value of intraoperative sonography during surgery for hepatic neoplasms," World J Surg, 2002, pp. 550-554, vol. 26—No. 5.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Zhang, Zhengyou, "A Flexible New Technique for Camera Calibration," 1998, pp. 1-21.
JP2009512514A: Included related PCT WO2007047782A2 instead of non-English language foreign reference JP2009512514A.
CN101193603A: Included related PCT WO2007030173A1 instead of non-English language foreign reference CN101193603A.
CN101291635A: Included related PCT WO2007047782A2 instead of non-English language foreign reference CN101291635A.
JP2009542362A: Included related PCT WO2008002830A2 instead of non-English language foreign reference JP2009542362A.
JPS61230895A: This reference was cited in the attached English language copy of a foreign search report or office action [Office Action mailed Sep. 3, 2014 for Japanese Application No. JP20120503535 filed Mar. 26, 2010 as supporting evidence that it was well known that when a plurality of manipulators are used for an operation, the manipulators may interfere, contact or collide with each other.
JPH01280449A—A translator's note at p. 3 (JP2009-518470 dated May 1, 2012) indicates that U.S. Pat. No. 5,748,767 is corresponding to Foreign Patent Document JPH01-280449A.
JP2001202531A—A translator'note at p. 4 (JP2013-186992 dated Jun. 12, 2015) indicates that U.S. Pat. No. 6,654,031 is an English language member of same patent family for Foreign Patent Document JP2001-202531A.
JPH08107875A—A translator's note at p. 4 (JP2013-186992 dated Jun. 12, 2015) indicates that U.S. Pat. No. 6,059,718 is an English language member of same patent family for Foreign Patent Document JPH08-107875A.

(56) References Cited

OTHER PUBLICATIONS

JP2002103258A—A translator's note at p. 5 (JP2013-186992 dated Jun. 12, 2015) indicates that U.S. Application Publication No. US20030023347 is an English language member of same patent family for Foreign Patent Document JP2002-103258A.

JPH07265321A—A translator's note at p. 5 (JP2013-186992 dated Jan. 26, 2015) indicates that European Patent Application Publication No. EP0646358A1 is an English language meber of same patent family for Foreign Patent Document JPH07-265321A.

Taylor, Russell H., Videotape: "Computer Assisted Surgery at IBM T. J. Watson Research Center," 22 minutes 10 seconds, 1994 and 1995.

Kato H., et al., "The Effects of Spatial Cues in Augmented Reality Video Conferencing," Hiroshima City University, Aug. 2001, 4 pages.

Kato H., et al. "Virtual Object Manipulation on a Table-Top AR Environment," Hiroshima City University, 2000, 9 pages.

Stoainovici D., et al., "Robotic Telemanipulation for Percutaneous Renal Access," in 16th World Congress on Endourology, New York City, Sep. 3-6, 1998, Poster Session 17-5, p. S201.

Office Action mailed Nov. 30, 2015 for Chinese Application No. 201280055140.8 filed Nov. 9, 2012, 12 pages.

Herper Matthew, "Watch a $1.5 Million Surgical Robot Play a Board Game," Forbes. Apr. 12, 2011, 2 pages, Online [Available: http://www.forbes.com/sites/matthewherper/2011/04/12/watch-a-1-5-million-surgical-robot-play-a-board-game/#587224f011f5] Accessed Jun. 7, 2016.

Office Action mailed Aug. 3, 2016 for Chinese Application No. 201280055140.8 filed Nov. 9, 2012, 9 pages.

Office Action mailed Nov. 22, 2016 for Japanese Application No. 2014-541311 filed Nov. 9, 2012, 16 pages.

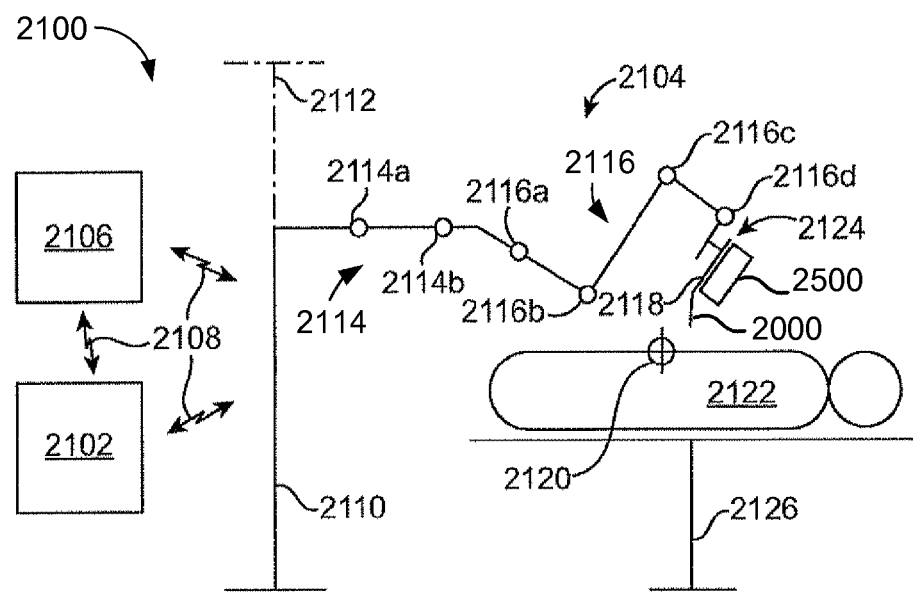
FIG.1
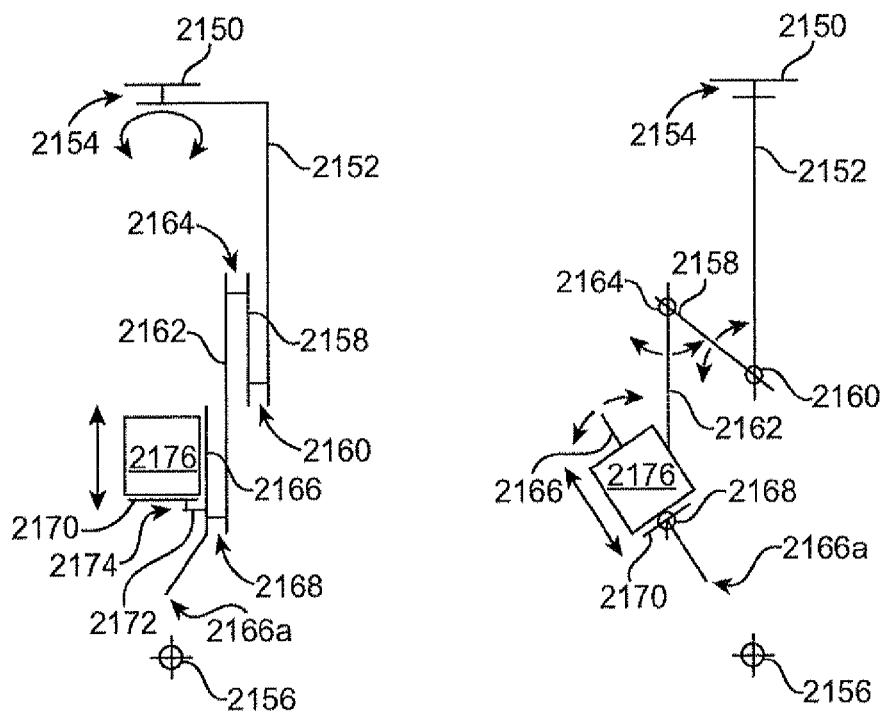
FIG.2
FIG.3

METHOD AND SYSTEM FOR MOVING AN ARTICULATED INSTRUMENT BACK TOWARDS AN ENTRY GUIDE WHILE AUTOMATICALLY RECONFIGURING THE ARTICULATED INSTRUMENT FOR RETRACTION INTO THE ENTRY GUIDE

CROSS REFERENCE TO RELATED APPLICATIONS

This application is a continuation to U.S. application Ser. No. 13/294,403, filed Nov. 11, 2011, which is a continuation-in-part to U.S. application Ser. No. 12/780,071, filed May 14, 2010, now U.S. Pat. No. 8,620,473, which is a continuation-in-part to U.S. application Ser. No. 11/762,200, filed Jun. 13, 2007, now U.S. Pat. No. 7,725,214, each of which is incorporated herein by reference.

This application is also a continuation-in-part to U.S. application Ser. No. 12/489,566, filed Nov. 5, 2009, now U.S. Pat. No. 9,089,256, which is incorporated herein by reference.

This application is also a continuation-in-part to U.S. application Ser. No. 12/613,328, filed Nov. 5, 2009, now U.S. Pat. No. 9,084,623, which is a continuation-in-part to U.S. application Ser. No. 12/541,913, filed Aug. 15, 2009, now U.S. Pat. No. 8,903,546, each of which is incorporated herein by reference.

FIELD OF THE INVENTION

The present invention generally relates to medical robotic systems and in particular, to a method and system for moving a plurality of articulated instruments in tandem back towards an entry guide out of which the plurality of articulated instruments extend.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the DA VINCI® Surgical System from Intuitive Surgical, Inc., of Sunnyvale, Calif., which is a minimally invasive robotic surgical system. The DA VINCI® Surgical System has a number of robotic arms that move attached medical devices, such as an image capturing device and Intuitive Surgical's proprietary ENDOWRIST® articulated surgical instruments, in response to movement of input devices operated by a Surgeon viewing images captured by the image capturing device of a surgical site. Each of the medical devices is inserted through its own minimally invasive incision into the Patient and positioned to perform a medical procedure at the surgical site. The incisions are placed about the Patient's body so that the surgical instruments may be used to cooperatively perform the medical procedure and the image capturing device may view it.

To perform certain medical procedures, however, it may be advantageous to use a single aperture, such as a minimally invasive incision or a natural body orifice, to enter a Patient to perform a medical procedure. For example, an entry guide (also referred to as a "guide tube") may first be inserted, positioned, and held in place in the entry aperture. Instruments such as an articulated camera and a plurality of articulated surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

U.S. 2009/0326318 A1 describes visual cues that aid an operator in repositioning the orientation of an entry guide so that the ranges of motion of articulated instruments extending out of its distal end may be optimized. U.S. 2011/0040305 A1 describes controller assisted reconfiguration of an articulated instrument during its movement into and out of an entry guide. U.S. 2011/0201883 A1 describes an entry guide for multiple instruments in a single port surgical system. U.S. 2008/0071288 A1 describes minimally invasive surgery guide tubes, articulated instruments extendable out of the guide tubes, and controllers for controlling movements of the guide tubes and instruments.

In addition to optimizing the ranges of motion of the articulated instruments, it may be necessary to change the orientation of the entry guide and consequently articulated instruments disposed therein so that one or more of the articulated instruments may reach or otherwise access a location within a Patient where a medical procedure is to be performed. When changing the orientation of the entry guide, however, care should be taken to ensure that the articulated instruments extending out of its distal end do not strike and harm surrounding tissue or other anatomical structures of the Patient. Also, haptic cues may be provided to assist a Surgeon during the entry guide re-orientation process.

OBJECTS AND SUMMARY

Accordingly, one object of one or more aspects of the present invention is a medical robotic system and method implemented therein that facilitates changing the orientation of an entry guide, through which articulated instruments are extendable, in a manner that avoids harming a Patient.

Another object of one or more aspects of the present invention is a medical robotic system and method implemented therein that facilitates changing the orientation of an entry guide, through which articulated instruments are extendable, in a quick and efficient manner that minimizes the steps to be performed by an operator of the medical robotic system.

Still another object of one or more aspects of the present invention is a medical robotic system and method implemented therein that facilitates operator controlled retraction of one or more articulated instruments into an entry guide as part of the process of re-orienting the entry guide or in other applications in which such controlled retraction is useful.

Yet another object of one or more aspects of the present invention is a medical robotic system and method implemented therein for retracting a plurality of articulated instruments in tandem back towards an entry guide out of which the plurality of articulated instruments extend.

These and additional objects are accomplished by the various aspects of the present invention, wherein briefly stated, one aspect is a method for moving a plurality of articulated instruments in tandem back towards an entry guide, the method comprising: causing the plurality of articulated instruments to assume retraction configurations only in response to one or more commands to move the plurality of articulated instruments in tandem back towards the entry guide by a distance greater than a retraction-on distance from an initial position.

Another aspect is a method for re-orienting an entry guide having a plurality of articulated instruments extending out of the entry guide, the method comprising: generating a first command to move the entry guide translationally along its longitudinal axis in a retraction direction by a distance exceeding a locking distance from an initial position; causing joints used for pivoting the entry guide to be locked in place in response to the first command; generating second commands to move the entry guide translationally along its longitudinal axis in the retraction direction by distances greater than a retraction-on distance from the initial position, wherein the retraction-on distance is greater than the locking distance; causing the plurality of articulated instruments to assume retraction configurations and be retracted in tandem back towards the entry guide in response to the second commands; causing the joints used for pivoting the entry guide to be unlocked after the plurality of articulated instruments has been retracted back towards the entry guide by a distance that allows pivoting of the entry guide without any of the plurality of articulated instruments harming any patient anatomy; generating third commands to pivot the entry guide to a different orientation; and causing the joints used for pivoting the entry guide to pivot the entry guide in response to the third commands.

Another aspect is a robotic system comprising: at least one input device; an entry guide; a plurality of articulated instruments extending out of a distal end of the entry guide; a plurality of instrument manipulators for manipulating corresponding ones of the plurality of articulated instruments; and a processor adapted to: command the plurality of instrument manipulators to manipulate the plurality of articulated instruments so as to assume retraction configurations in response to one or more commands received from the at least one input device to move the plurality of articulated instruments in tandem back towards the entry guide by a distance greater than a retraction-on distance from an initial position.

Additional objects, features and advantages of the various aspects of the present invention will become apparent from the following description of its preferred embodiment, which description should be taken in conjunction with the accompanying drawings.

BRIEF DESCRIPTION OF THE DRAWINGS

FIG. 1 illustrates a schematic view of a medical robotic system utilizing aspects of the present invention.

FIGS. 2 and 3 respectively illustrate alternative embodiments of a Patient side support system useful in a medical robotic system utilizing aspects of the present invention.

DETAILED DESCRIPTION

FIG. 1 illustrates, as an example, a schematic view of a medical robotic system 2100 in which instruments are inserted in a Patient through a single entry aperture through an entry guide. The system's general architecture is similar to the architecture of other such systems such as Intuitive Surgical, Inc.'s DA VINCI® Surgical System and the ZEUS® Surgical System. The three main components are a Surgeon console 2102, a Patient side support system 2104, and a video system 2106, all interconnected by wired or wireless connections 2108 as shown.

The Patient side support system 2104 includes a floor-mounted structure 2110, or alternately a ceiling mounted structure 2112 as shown by the alternate lines. It also includes a set-up arm assembly 2114, an entry guide manipulator (EGM) 2116, a platform 2118, an entry guide (EG) 2000, and one or more instrument assemblies 2500. The structure 2110 may be movable or fixed (e.g., to the floor, ceiling, or other equipment such as an operating table). In one embodiment, the set-up arm assembly 2114 includes two illustrative passive rotational setup joints 2114a, 2114b, which allow manual positioning of the coupled links when their brakes are released. A passive prismatic setup joint (not shown) between the arm assembly 2114 and the structure 2110 may be used to allow for large vertical adjustments.

Figure 4:
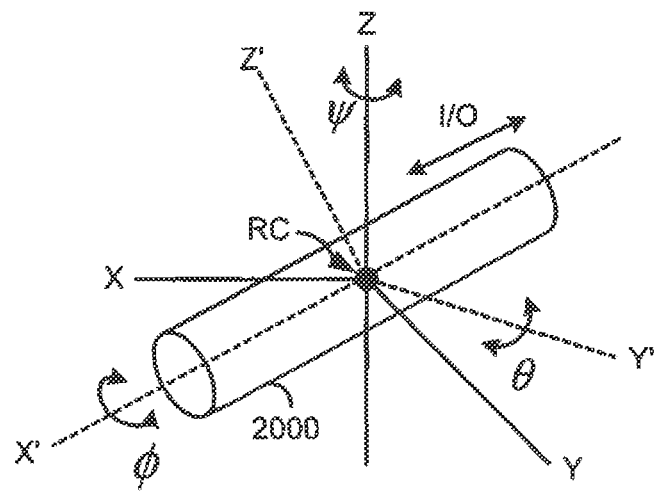
FIG. 4 illustrates reference frames and degrees-of-freedom associated with manipulation of an entry guide in a medical robotic system utilizing aspects of the present invention.

The entry guide 2000 is coupled to the platform 2118, which in turn, is coupled to the entry guide manipulator 2116 so that the entry guide manipulator 2116 may pivot the platform 2118, which in turn, causes the entry guide 2000 to pivot about a Remote Center (RC) point. As shown in a perspective view of the entry guide 2000 in FIG. 4, the entry guide 2000 is generally cylindrical in shape and has a longitudinal axis X' running centrally along its length. The RC point serves as an origin for both a fixed reference frame having X, Y and Z axes as shown and an entry guide reference frame having X', Y' and Z' axes as shown. When the system 2100 is in an "entry guide" mode, the entry guide manipulator 2116 pivots the entry guide 2000, in response to movement of one or more associated input devices commanding such pivoting, about the Z axis (which remains fixed in space) at the RC point in yaw $\psi$. In addition, the entry guide manipulator 2116 pivots the entry guide 2000, in response to movement of the one or more input devices commanding such pivoting, about the Y' axis (which is orthogonal to the longitudinal axis X' of the entry guide 2000) in pitch $\theta$; rotates the entry guide 2000, in response to movement of the one or more input devices commanding such rotation, about its longitudinal axis X' in roll $\Phi$; and optionally, linearly moving the entry guide 2000, in response to movement of the one or more input devices commanding such movement, along its longitudinal axis X' in insertion/retraction or in/out "I/O" directions. Note that unlike the Z-axis which is fixed in space, the X' and Y' axes move with the entry guide 2000.

The entry guide manipulator 2116 includes illustrative active (i.e., actuatable) yaw joint 2116a and active pitch joint 2116b. Joints 2116c and 2116d act as a parallel mechanism so that the entry guide 2000 being held by the platform 2118 may pivot in yaw and pitch about the RC point which is positioned at an entry port 2120, such as an umbilicus of Patient 2122, prior to the performance of a medical procedure using the set-up arm assembly 2114. In one embodiment, an active prismatic joint 2124 may be used to insert and retract the entry guide 2000. One or more instrument assemblies 2500 such as assemblies for surgical instruments and an endoscopic imaging system are independently mounted to platform 2118 so as to be disposed within and extendable through the entry guide 2000.

Thus, the set-up arm assembly 2114 is used to position the entry guide 2000 in the entry port 2120 of the Patient 2122 when the Patient 2122 is placed in various positions on movable table 2126. After set-up of the entry guide 2000, instrument assemblies 2500 are mounted on the platform 2118 so that their articulated instruments extend into the entry guide 2000. The entry guide manipulator 2116 may then be used to pivot the entry guide 2000 and the articulated instruments disposed therein about the RC point in pitch and yaw. Rotation of the entry guide 2000 and/or insertion/retraction of the entry guide 2000 by the entry guide manipulator 2116 do not necessarily result in corresponding movement of the articulated instruments disposed therein, however.

Figure 5:
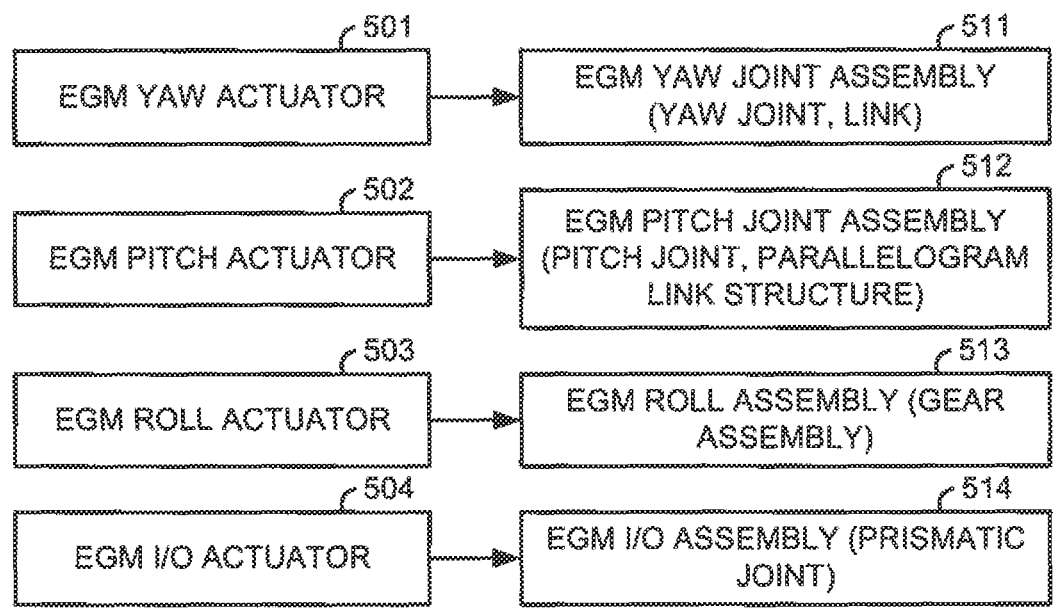
FIG. 5 illustrates a block diagram of components of an entry guide manipulator for manipulating an entry guide in a medical robotic system utilizing aspects of the present invention.

As shown in FIG. 5, the entry guide manipulator (EGM) 2116 has four actuators 501-504 for actuating the four degrees-of-freedom movement of the entry guide 2000 (i.e., yaw $\psi$, pitch $\theta$, roll $\Phi$, and in/out I/O) and four corresponding assemblies 511-514 to implement them. The EGM yaw assembly 511 includes the yaw rotary joint 2116a and one or more links that couple it through other parts of the entry guide manipulator 2116 to the platform 2118 so that when the EGM yaw actuator 501 (e.g., a motor) actuates (e.g., rotates) the yaw rotary joint, the entry guide 2000 is rotated about the fixed Z-axis at the RC point in yaw $\psi$. The EGM pitch assembly 512 includes the pitch rotary joint 2116b and one or more links that couple it through other parts of the entry guide manipulator 2116 to the platform 2118 so that when the EGM pitch actuator 502 (e.g., a motor) actuates (e.g., rotates) the pitch rotary joint, the entry guide 2000 is rotated about the Y'-axis at the RC point in pitch $\theta$. The EGM roll assembly 513 includes a gear assembly that couples the entry guide 2000 to an EGM roll actuator 503 so that when the EGM roll actuator 503 (e.g., a motor) actuates (e.g., its rotor rotates), the entry guide 2000 rotates about its longitudinal axis X' in response. In one embodiment, the EGM I/O assembly 514 includes a prismatic joint that is coupled to the EGM I/O actuator 504 so that when the EGM I/O actuator 504 (e.g., a motor) actuates (e.g., its rotor rotates), the rotary action is transferred into a linear displacement of the entry guide 2000 along its longitudinal axis X'. In another embodiment, rather than moving the entry guide 2000 in the insertion/retraction direction, all articulated instruments disposed in the entry guide 2000 are moved instead in the insertion/retraction direction in response to an EG I/O command.

FIGS. 2 and 3 illustrate, as examples, alternative embodiments of the Patient side support system 2104. Support 2150 is fixed (e.g., floor or ceiling mounted). Link 2152 is coupled to support 2150 at passive rotational setup joint 2154. As shown, joint 2154's rotational axis is aligned with RC point 2156, which is generally the position at which an entry guide (not shown) enters the Patient (e.g., at the umbilicus for abdominal surgery). Link 2158 is coupled to link 2152 at rotational joint 2160. Link 2162 is coupled to link 2158 at rotational joint 2164. Link 2166 is coupled to link 2162 at rotational joint 2168. The entry guide is mounted to slide through the end 2166a of link 2166. Platform 2170 is supported and coupled to link 2166 by a prismatic joint 2172 and a rotational joint 2174. Prismatic joint 2172 inserts and retracts the entry guide as it slides along link 2166. Joint 2174 includes a bearing assembly that holds a "C" shaped ring cantilever. As the "C" ring slides through the bearing it rotates around a center point inside the "C", thereby rolling the entry guide. The opening in the "C" allows entry guides to be mounted or exchanged without moving overlying manipulators. Platform 2170 supports multiple instrument manipulators 2176 for surgical instruments and an imaging system, as described below.

These illustrative robotic arm assemblies (i.e., set-up arm assemblies and entry guide manipulators) are used, for example, for instrument assemblies that include a rigid entry guide and are operated to move with reference to a Remote Center (RC) point. Certain setup and active joints in the robotic arm assemblies may be omitted if motion around a remote center is not required. It should be understood that set-up and manipulator arms may include various combinations of links, passive, and active joints (redundant DOFs may be provided) to achieve a necessary range of poses for surgery.

Referring again to FIG. 1, the video system 2106 performs image processing functions for, e.g., captured endoscopic imaging data of the surgical site and/or preoperative or real time image data from other imaging systems external to the Patient. Video system 2106 outputs processed image data (e.g., images of the surgical site, as well as relevant control and Patient information) to the Surgeon at the Surgeon console 2102. In some aspects the processed image data is output to an optional external monitor visible to other operating room personnel or to one or more locations remote from the operating room (e.g., a Surgeon at another location may monitor the video; live feed video may be used for training; etc.).

Figure 6:
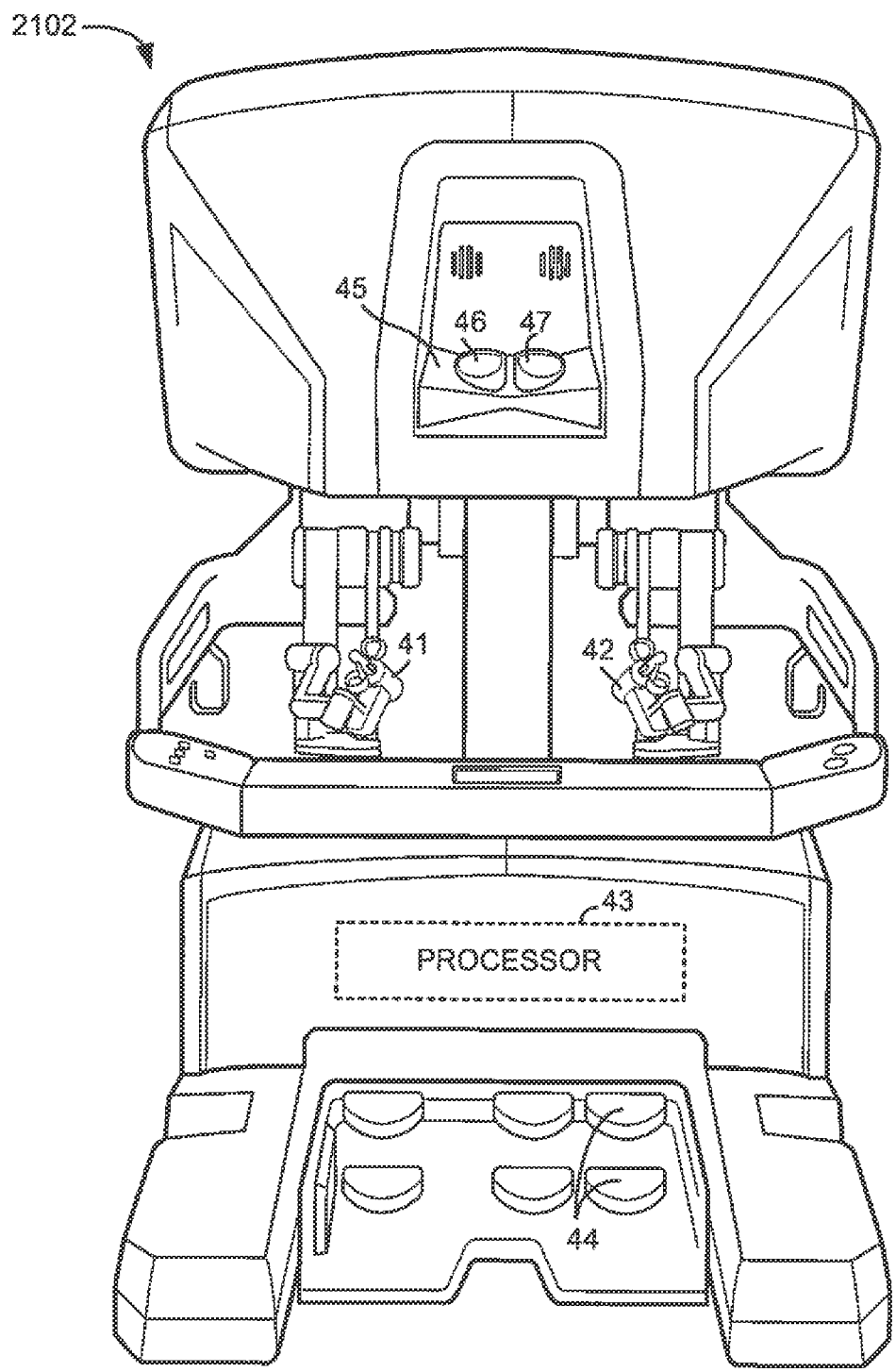
FIG. 6 illustrates a front view of a Surgeon console useful in a medical robotic system utilizing aspects of the present invention.

FIG. 6 illustrates, as an example, a front view of the Surgeon console 2102 which a Surgeon or other user operates for controlling movement of the entry guide and articulated instruments of the system 2100. The Surgeon console 2102 has left and right input devices 41, 42 which the user may grasp respectively with his/her left and right hands to manipulate associated devices, such as the entry guide and articulated instruments, in preferably six degrees-of-freedom. Foot pedals 44 with toe and heel controls are provided on the Surgeon console 2102 so the user may control movement and/or actuation of devices associated with the foot pedals. A processor 43 is provided in the Surgeon console 2102 for control and other purposes. Although shown as a single processor located in the base of the Surgeon console 2102, the processor 43 may be implemented as multiple cooperative processors distributed in the Surgeon console 2102 as well as other parts of the medical robotic system 2100. A stereo viewer 45 is also provided in the Surgeon console 2102 so that the user may view the work site in stereo vision from images captured by a stereoscopic camera of an articulated camera instrument. Left and right eyepieces, 46 and 47, are provided in the stereo viewer 45 so that the user may view left and right 2-D display screens inside the viewer 45 respectively with the user's left and right eyes.

The Surgeon console 2102 is usually located in the same room as the Patient 2122 so that the Surgeon may directly monitor the procedure, is physically available if necessary, and is able to speak to any assistants in the operating room directly rather than over the telephone or other communication medium. However, it will be understood that the Surgeon can also be located in a different room, a completely different building, or other remote location from the Patient allowing for remote surgical procedures.

Figure 7:
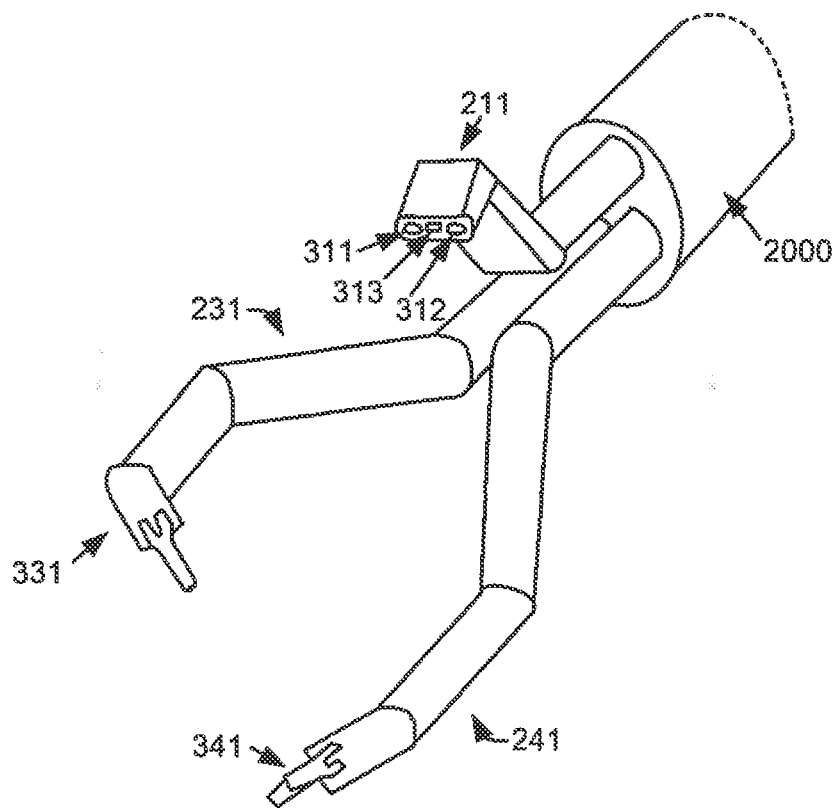
FIG. 7 illustrates a perspective view of a distal end of an entry guide with articulated instruments extending out of it in a medical robotic system utilizing aspects of the present invention.
Figure 8:
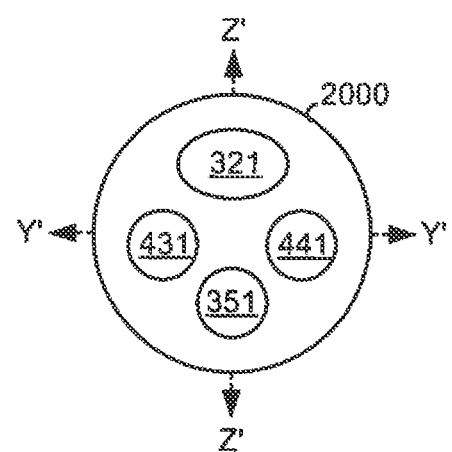
FIG. 8 illustrates a cross-sectional view of an entry guide useful in a medical robotic system utilizing aspects of the present invention.

As shown in FIG. 7, the entry guide 2000 has articulated instruments such as articulated surgical tool instruments 231, 241 and an articulated stereo camera instrument 211 (or other image capturing device instrument) extending out of its distal end. The camera instrument 211 has a pair of stereo image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 2000 may guide additional tools as required for performing a medical procedure at a work site in the Patient. For example, as shown in FIG. 8, a passage 351 is available for extending another articulated surgical tool through the entry guide 2000 and out through its distal end. Passages 431, 441, and 321 are respectively used by the articulated surgical tool instruments 231, 241, and articulated camera instrument 211. Each of the surgical tools 231, 241 is associated with one of the input devices 41, 42 in a tool following mode. The Surgeon performs a medical procedure by manipulating the input devices 41, 42 so that the controller 43 causes corresponding movement of their respectively associated surgical tools 231, 241 while the Surgeon views the work site in 3-D on the console stereo viewer 45 as images of the work site are being captured by the articulated camera instrument 211.

Preferably, input devices 41, 42 will be provided with at least the same degrees of freedom as their associated tools 231, 241 to provide the Surgeon with telepresence, or the perception that the input devices 41, 42 are integral with the tools 231, 241 so that the Surgeon has a strong sense of directly controlling the tools 231, 241. To this end, the stereo viewer 45 is also positioned near the Surgeon's hands as shown so that it will display a projected image that is oriented so that the Surgeon feels that he or she is actually looking directly down onto the work site and images of the tools 231, 241 appear to be located substantially where the Surgeon's hands are located.

In addition, the real-time image on the stereo viewer 45 is preferably projected into a perspective image such that the Surgeon can manipulate the end effectors 331, 341 of the tools 231, 241 through their corresponding input devices 41, 42 as if viewing the work site in substantially true presence. By true presence, it is meant that the presentation of an image is a true perspective image simulating the viewpoint of an operator that is physically manipulating the end effectors 331, 341. Thus, the processor 43 transforms the coordinates of the end effectors 331, 341 to a perceived position so that the perspective image being shown on the stereo viewer 45 is the image that the Surgeon would see if the Surgeon was located directly behind the end effectors 331, 341.

The processor 43 performs various functions in the system 2100. One important function that it performs is to translate and transfer the mechanical motion of input devices 41, 42 through control signals over communication means 2108 to actuate actuators in their associated manipulators so that the Surgeon can effectively manipulate devices, such as the tool instruments 231, 241, camera instrument 211, and entry guide 2000. Another function is to perform various methods and implement various controllers and coupling logic described herein.

Although described as a processor, it is to be appreciated that the processor 43 may be implemented by any combination of hardware, software and firmware. Also, its functions as described herein may be performed by one unit or divided up among different components, each of which may be implemented in turn by any combination of hardware, software and firmware. Further, although being shown as part of or being physically adjacent to the console 2102, the processor 43 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus"; U.S. Pat. No. 6,671,581 "Camera Referenced Control in a Minimally Invasive Surgical Apparatus"; and U.S. 2008/0071288 A1 "Minimally Invasive Surgery Guide Tube"; each of which is incorporated herein by reference.

Figure 9:
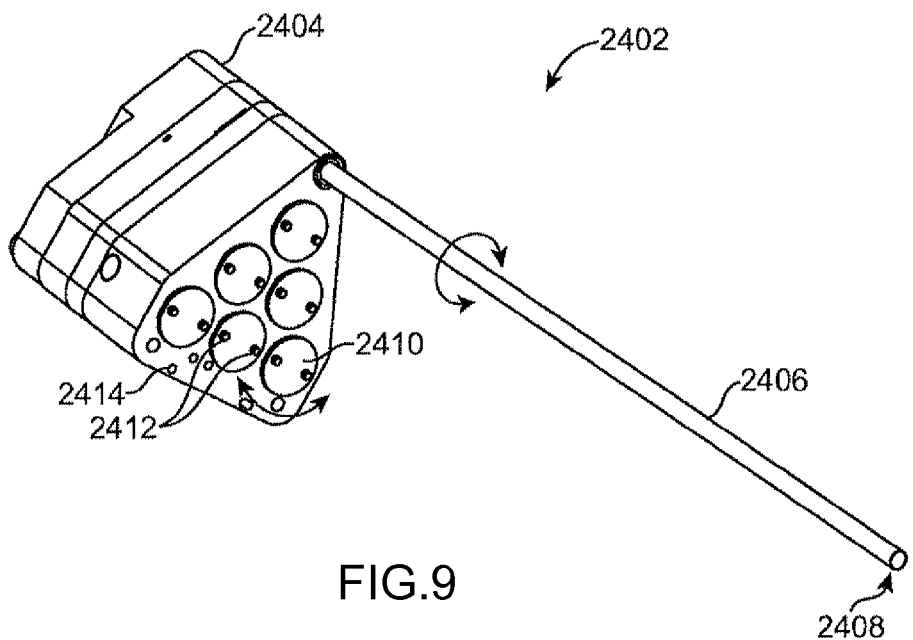
FIG. 9 illustrates a perspective view of a proximal segment of an articulated instrument useful in a medical robotic system utilizing aspects of the present invention.

Mounting of the instrument assemblies 2500 onto the platform 2118 with their working ends inserted into the entry guide 2000 is now described in reference to FIGS. 9-12. As shown in FIG. 9, articulated instrument 2402 includes a transmission mechanism 2404 coupled to the proximal end of an instrument body tube 2406. Components at body tube 2406's distal end 2408 are omitted for clarity and may include actuatable joints and working ends as shown in FIG. 7. In the illustrative embodiment shown, transmission mechanism 2404 includes six interface disks 2410. Each of the disks 2410 may be associated with a Degree-of-Freedom (DOF) for the articulated instrument 2402. For instance, one disk may be associated with instrument body roll DOF, and a second disk may be associated with end effector grip DOF. As shown, in one instance the disks are arranged in a hexagonal lattice for compactness—in this case six disks in a triangular shape. Other lattice patterns or more arbitrary arrangements may be used. Mechanical components (e.g., gears, levers, gimbals, cables, etc.) inside transmission mechanism 2404 transmit roll torques on disks 2410 to e.g., body tube 2406 (for roll) and to components coupled to distal end mechanisms. Cables and/or cable and hypotube combinations that control distal end DOFs run through body tube 2406. In one instance the body tube is approximately 7 mm in diameter, and in another instance it is approximately 5 mm in diameter. Raised pins 2412, spaced eccentrically, provide proper disk 2410 orientation when mated with an associated actuator disk. One or more electronic interface connectors 2414 provide an electronic interface between instrument 2402 and its associated actuator mechanism. The electronic interface may also include power for, e.g., an electrocautery end effector. Alternately, such a power connection may be positioned elsewhere on instrument 2402 (e.g., on transmission mechanism 2404's housing). Other connectors for, e.g., optical fiber lasers, optical fiber distal bend or force sensors, irrigation, suction, etc. may be included. As shown, transmission mechanism 2404's housing is roughly wedge or pie-shaped to allow it to be closely positioned to similar housings, as illustrated below.

Figure 10:
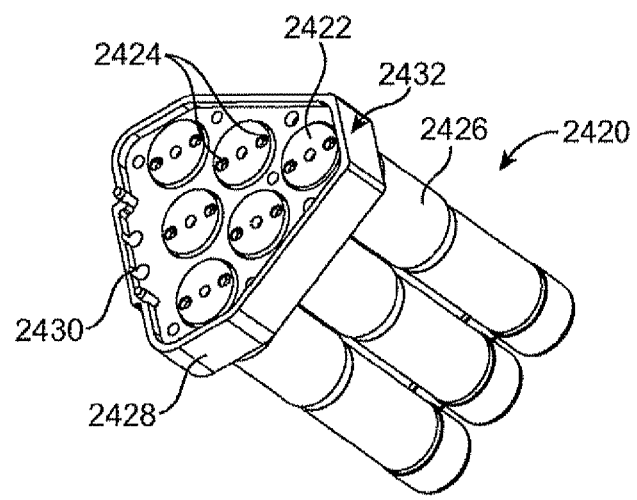
FIG. 10 illustrates a perspective view of a segment of an actuator assembly of an instrument manipulator that mates with and actuates an articulated instrument useful in a medical robotic system utilizing aspects of the present invention.

FIG. 10 is a perspective view of a portion of an actuator assembly 2420 (also referred to herein as an instrument "manipulator") that mates with and actuates components in surgical instrument 2402. Actuator disks 2422 are arranged to mate with interface disks 2410. Holes 2424 in disks 2422 are aligned to receive pins 2412 in only a single 360-degree orientation. Each disk 2422 is turned by an associated rotating servomotor actuator 2426, which receives servocontrol inputs from its respective controller as described below. A roughly wedge-shaped mounting bracket 2428, shaped to correspond to instrument 2402's transmission mechanism housing, supports the disks 2422, servomotor actuators 2426, and an electronic interface 2430 that mates with instrument 2402's interface connectors 2414. In one instance instrument 2402 is held against actuator assembly 2420 by spring clips (not shown) to allow easy removal. As shown in FIG. 10, a portion 2432 of actuator assembly housing 2428 is truncated to allow instrument body tube 2406 to pass by. Alternatively, a hole may be placed in the actuator assembly to allow the body tube to pass through.

Figure 11:
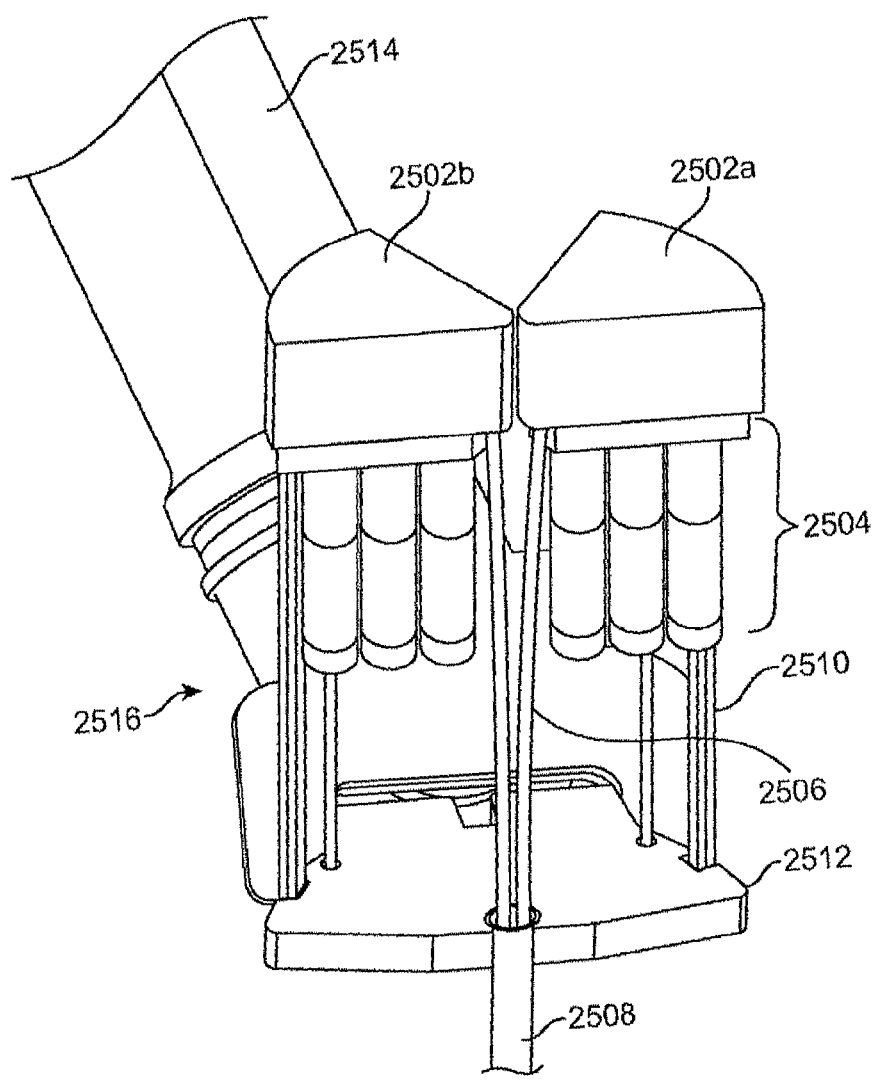
FIG. 11 illustrates a first perspective view of articulated instrument assemblies mounted on a platform coupled to a robotic arm assembly in a medical robotic system utilizing aspects of the present invention.

FIG. 11 is a diagrammatic perspective view that illustrates aspects of mounting minimally invasive surgical instruments and their associated actuator assemblies at the end of a setup/manipulator arm. As shown in FIG. 11, surgical instrument 2502*a* is mounted on actuator assembly 2504, so that the transmission mechanism mates with the actuator assembly as described above. Instrument 2502*a*'s body tube 2506 extends past actuator assembly 2504 and enters a port in rigid entry guide 2508. As depicted, body tube 2506, although substantially rigid, is bent slightly between the transmission mechanism housing and the entry guide. This bending allows the instrument body tube bores in the entry guide to be spaced closer than the size of their transmission mechanisms would otherwise allow. Since the bend angle in the rigid instrument body tube is less than the bend angle for a flexible (e.g., flaccid) instrument body, cables can be stiffer than in a flexible body. High cable stiffness is important because of the number of distal DOFs being controlled in the instrument. Also, the rigid instrument body is easier to insert into an entry guide than a flexible body. In one embodiment the bending is resilient so that the body tube assumes its straight shape when the instrument is withdrawn from the entry guide (the body tube may be formed with a permanent bend, which would prevent instrument body roll). Actuator assembly 2504 is mounted to a linear actuator 2510 (e.g. a servocontrolled lead screw and nut or a ball screw and nut assembly) that controls body tube 2506's insertion within entry guide 2508. The second instrument 2502*b* is mounted with similar mechanisms as shown. In addition, an imaging system (not shown) may be similarly mounted.

FIG. 11 further shows that entry guide 2508 is removably mounted to support platform 2512. This mounting may be, for example, similar to the mounting used to hold a cannula on a DA VINCI® Surgical System manipulator arm. Removable and replaceable entry guides allow different entry guides that are designed for use with different procedures to be used with the same telemanipulative system (e.g., entry guides with different cross-sectional shapes or various numbers and shapes of working and auxiliary channels). In turn, actuator platform 2512 is mounted to robot manipulator arm 2514 (e.g., 4 DOF) using one or more additional actuator mechanisms (e.g., for pitch, yaw, roll, insertion). In turn, manipulator arm 2514 may be mounted to a passive setup arm, as described above with reference to the entry guide manipulator 2116 of FIG. 1.

Figure 12:
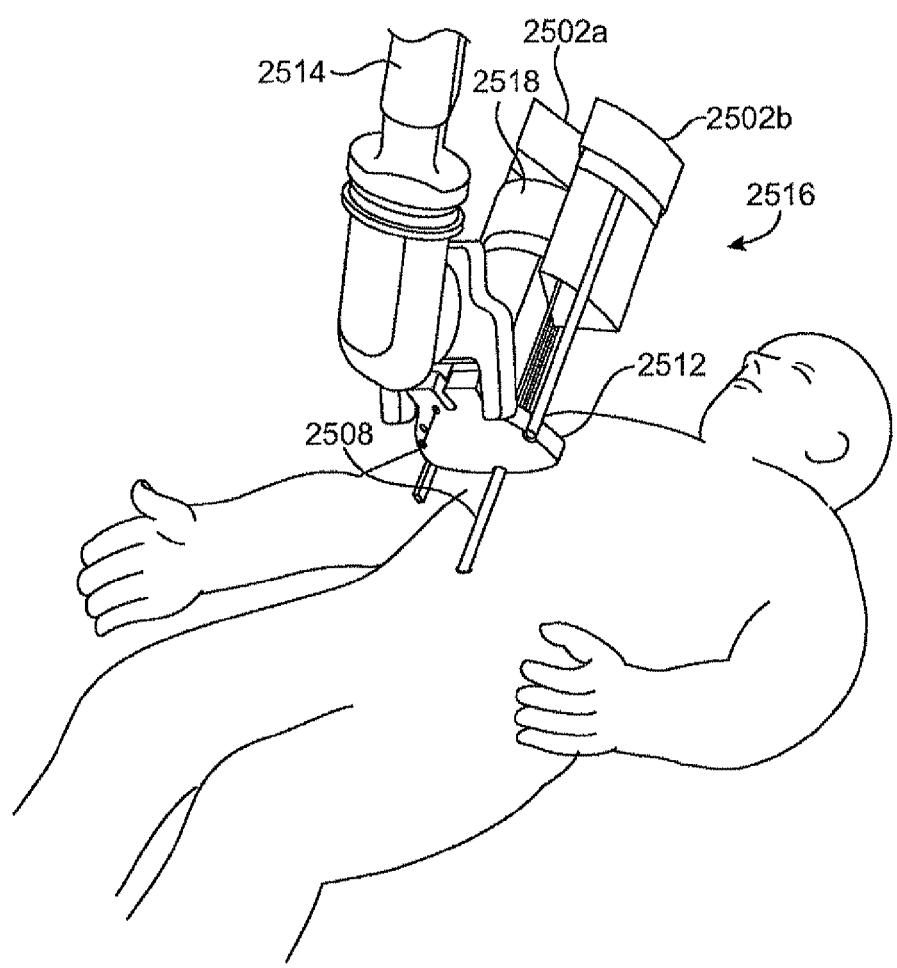
FIG. 12 illustrates a second perspective view of articulated instruments assemblies mounted on a platform coupled to a robotic arm assembly in a medical robotic system utilizing aspects of the present invention.

FIG. 12 is a diagrammatic perspective view that illustrates aspects shown in FIG. 11 from a different angle and with reference to a Patient. In FIG. 12, arm 2514 and platform 2512 are positioned so that entry guide 2508 enters the Patient's abdomen at the umbilicus. This entry is illustrative of various natural orifice and incision entries, including percutaneous and transluminal (e.g., transgastric, transcolonic, transrectal, transvaginal, transrectouterine (Douglas pouch), etc.) incisions. FIG. 12 also illustrates how the linear actuators for each instrument/imaging system operate independently by showing imaging system 2518 inserted and instruments 2502*a*, 2502*b* withdrawn. It can be seen that in some instances the manipulator arm 2514 moves to rotate or pivot entry guide 2508 around a Remote Center (RC) 2520 at the entry port into a Patient. If intermediate tissue restricts movement around a remote center, however, the arm can maintain entry guide 2508 in position.

Figure 13:
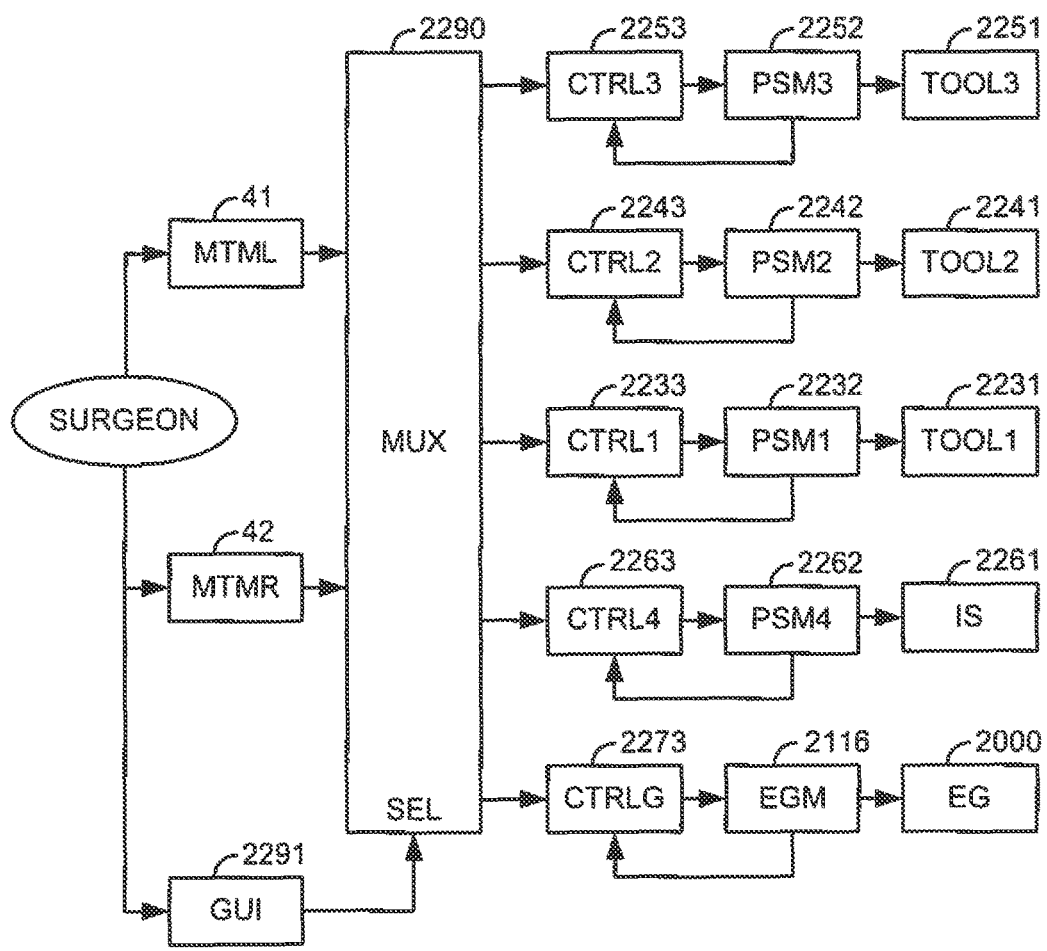
FIG. 13 illustrates a block diagram of components for controlling and selectively associating controllable devices with input devices of a medical robotic system utilizing aspects of the present invention.

FIG. 13 illustrates, as an example, a block diagram of components used for controlling and selectively associating articulated instruments on the Patient side support system 2104 to operator manipulated input devices 41, 42 of the Surgeon console 2102. Various surgical tools such as graspers, cutters, and needles may be used to perform a medical procedure at a work site within the Patient. In this example, three articulated surgical tool instruments (TOOL1, TOOL2, TOOL3) 2231, 2241, 2251 are used to robotically perform the procedure and an articulated imaging system instrument (IS) 2261 is used to view the procedure. In other examples, more or less instruments may be used. The imaging system 2261 may be a stereoscopic camera instrument, such as camera instrument 211, or another type of imaging system such as a monoscopic camera instrument or an ultrasound probe instrument. The tools 2231, 2241, 2251 and imaging system 2261 may be disposed in an entry guide (EG) 2000 so as to be extendable beyond a distal end of the entry guide 2000. The entry guide 2000 may be inserted into the Patient through an entry aperture such as a minimally invasive incision or a natural orifice using the setup portion of a robotic arm assembly and maneuvered by an entry guide manipulator (EGM) 2116 towards the work site where the medical procedure is to be performed.

Each of the devices 2231, 2241, 2251, 2261, 2000 is manipulated by its own manipulator. In particular, the imaging system (IS) 2261 is manipulated by an imaging system manipulator (PSM4) 2262, the first surgical tool (TOOL1) 2231 is manipulated by a first tool manipulator (PSM1) 2232, the second surgical tool (TOOL2) 2241 is manipulated by a second tool manipulator (PSM2) 2242, the third surgical tool (TOOL3) 2251 is manipulated by a third tool manipulator (PSM3) 2252, and the entry guide (EG) 2000 is manipulated by the entry guide manipulator (EGM) 2116.

Each of the instrument manipulators 2232, 2242, 2252, 2262 is a mechanical assembly that carries actuators and provides a mechanical, sterile interface to transmit motion to its respective articulated instrument. Each of the articulated instruments 2231, 2241, 2251, 2261 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

In direct control mode, each of the input devices 41, 42 may be selectively associated with one of the devices 2261, 2231, 2241, 2251, 2000 through a multiplexer (MUX) 2290 so that the associated device may be controlled by the input device through its controller and manipulator. For example, the Surgeon may specify the association through a graphical user interface (GUI) 2291 on the Surgeon console 2102 for the left and right input devices 41, 42 to be respectively associated with the first and second surgical tools 2231, 2241, which are telerobotically controlled through their respective controllers 2233, 2243 and manipulators 2232, 2242 so that the Surgeon may perform a medical procedure on the Patient while the surgical tool 2251, imaging system 2261 and entry guide 2000 are each soft locked in place through their respective controllers. If the Surgeon desires to control movement of the surgical tool 2251 using one of the input devices 41, 42, then the Surgeon may do so by simply disassociating the input device from its currently associated device and associating it instead to the tool 2251. Likewise, if the Surgeon desires to control movement of either the imaging system 2261 or entry guide 2000 using one or both of the input devices 41, 42, then the Surgeon may do so by simply disassociating the input device from its currently associated device and associating it instead to the imaging system 2261 or entry guide 2000.

As alternatives to using the GUI 2291 for providing selection input SEL for the MUX 2290, the selective association of the input devices 41, 42 to devices 2251, 2241, 2231, 2261, 2000 may be performed by the Surgeon using voice commands understood by a voice recognition system, or by the Surgeon depressing a button on one of the input devices 41, 42, or by the Surgeon depressing a foot pedal on the Surgeon console 2102, or by the Surgeon using any other well known mode switching technique. Although such mode switching is described herein as being performed by the Surgeon, it may alternatively be performed by an Assistant under the direction of the Surgeon.

Each of the controllers 2233, 2243, 2253, 2263, 2273 comprises a master/slave control system that includes a joint controller for each joint of its respective articulated instrument or in the case of the entry guide 2000, its manipulator 2116. To simplify the description herein and in the claims, the term "joint" is to be understood as a connection (translational or revolute) between two links, and may include gears (or prismatic joints) as well as any other controllable component coupled to linear drive mechanisms that may be used in controlling robotic arm assemblies. An example of such a control system is described in previously incorporated by reference and U.S. Pat. No. 6,424,885, "Camera Referenced Control in a Minimally Invasive Surgical Apparatus."

Direct control modes are control modes in which the user has direct control over a specific slave manipulator. All other slave manipulators (i.e., the ones that are not connected to an input device) may be soft-locked (i.e., all their joints are held in place by their respective controllers). As an example, in a single-port system such as described herein, three direct control modes are defined as a direct "tool following" mode in which the two hand-operable input devices are associated with two tool slave manipulators and their respective tools, a direct "imaging system" mode in which one or both of the hand-operable input devices are associated with the imaging system, and a direct "entry guide" mode in which one or both hand-operable input devices are associated with the entry guide.

In a coupled control mode, the Surgeon is directly controlling movement of an associated slave manipulator (e.g., one of the manipulators 2232, 2242, 2252, 2262, 2116) while indirectly controlling movement of one or more non-associated slave manipulators, in response to commanded motion of the directly controlled slave manipulator, to achieve a secondary objective. By automatically performing secondary tasks through coupled control modes, the system's usability is enhanced by reducing the Surgeon's need to switch to another direct mode to manually achieve the desired secondary objective. Thus, coupled control modes allow the Surgeon to better focus on performing the medical procedure and to pay less attention to managing the system.

The GUI 2291 used by the Surgeon to specify the association of inputs devices 41, 42 and devices 2231, 2241,

2251, 2261, 2000 may also be used by the Surgeon to specify various parameters of the coupled control modes. For example, the Surgeon may use the GUI 2291 to select which device manipulators participate in various coupled control modes and to define and/or prioritize the secondary objectives associated with the coupled control modes.

In "entry guide" mode, both input devices 41, 42 may be used to move the entry guide 2000 as the Surgeon views on the stereo viewer 45 processed images that were originally captured by the camera 211. An image referenced control is implemented in the entry guide controller 2273 so that the controller 2273 controls movement of the entry guide 2000 while the Surgeon is given the impression that he or she is moving the image captured by the camera 211. In particular, the Surgeon is provided with the sensation that he or she is grasping the image being displayed on the viewer 45 with his or her left and right hands and moving the image about the work site to a desired viewing point. Note that under this control, the image on the viewer 45 appears to move in opposite directions in response to movement of the input devices 41, 42. For example, the image moves to the right when the input devices 41, 42 move to the left (and vice versa). Also, the image moves up when the input devices 41, 42 are moved down (and vice versa). Pivoting of the entry guide is accomplished using a "virtual handlebar" in which pivot points of the left and right input devices 41, 42 define a handle bar axis which passes through the pivot points. An entry guide yaw command may then be generated by the Surgeon moving one input device forward while moving the other one back. An entry guide pitch command, on the other hand, may be generated by the Surgeon pivoting both input devices about the handle bar axis in the same direction (either up to pitch up or down to pitch down). An entry guide roll command may be generated by the Surgeon moving one input device up while moving the other input device down. An insertion command may be generated by the Surgeon moving both input devices backward and a retraction command may be generated by the Surgeon moving both input device forward.

Figure 14:
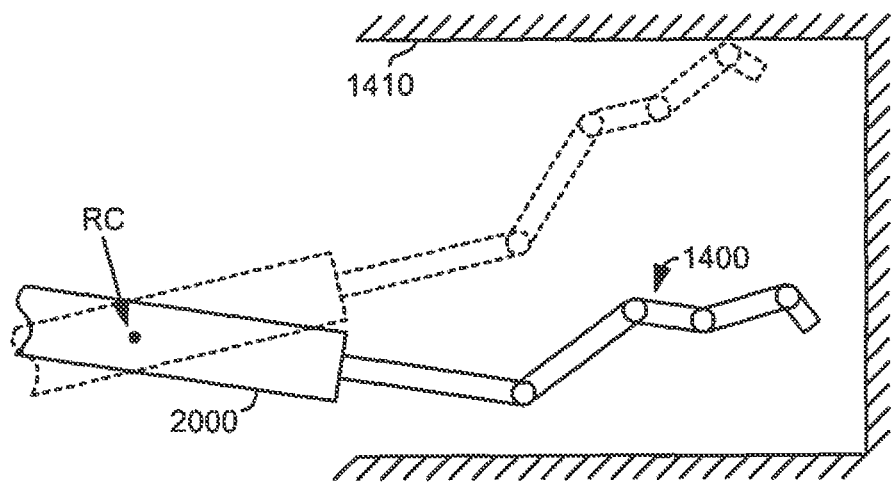
FIG. 14 illustrates a side view of a pivoting entry guide with an articulated instrument extending out of its distal end in a medical robotic system utilizing aspects of the present invention.
Figure 15:
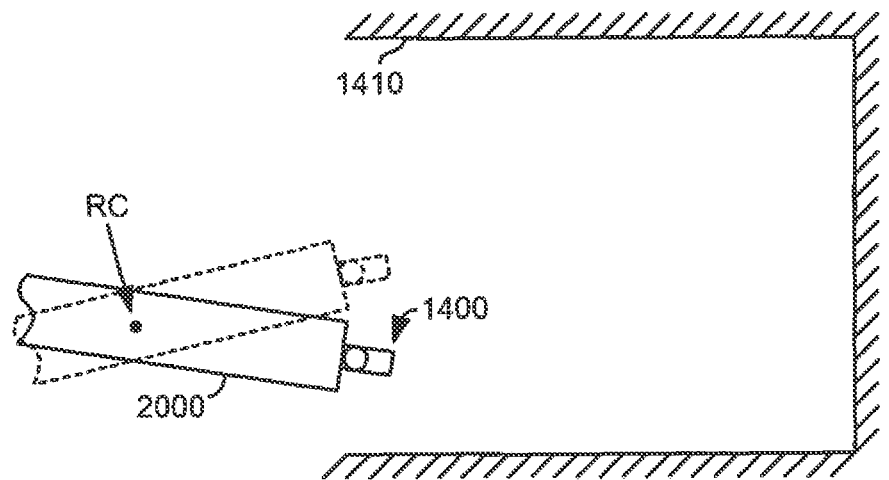
FIG. 15 illustrates a side view of a pivoting entry guide with an articulated instrument retracted into the entry guide in a medical robotic system utilizing aspects of the present invention.

When the Surgeon is operating in the "entry guide" mode to re-orient the entry guide 2000 along with all of the articulated instruments within it at the time, the Surgeon may inadvertently strike and harm the patient's anatomy with an articulated instrument that is extending out of the distal end of entry guide when the entry guide is being pivoted about its Remote Center (RC). For example, referring to FIG. 14, an articulated instrument 1400 is shown in solid line form extending out of the distal end of the entry guide 2000 at an initial orientation and shown in dotted line form striking the patient anatomy 1410 after being pivoted about the RC point. Although a distal end of the articulated instrument is shown as striking the patient anatomy in this example, in practice, it is to be appreciated that other parts of an articulated instrument such as more proximal (i.e., closer to the entry guide) links of the articulated instruments 211, 231, 241 may also potentially strike patient anatomy due to the articulated nature of the instruments. In addition, it may be difficult for a Surgeon to foresee such striking when viewing the work site on the stereo viewer 45 since the proximal links may be out of the field of view of the camera instrument 211. Thus, to avoid inadvertently striking and harming the patient anatomy, it is advisable to retract all articulated instruments back into the entry guide before re-orienting the entry guide, such as shown, for example, in FIG. 15, when large adjustments to the orientation of the entry guide 2000 are being made.

When there is a plurality of articulated instruments extending out of the entry guide 2000, such as shown in FIG. 7, it may be tedious and time consuming for the Surgeon to change modes between "entry guide" and "tool following" modes, place the articulated instruments one-at-a-time into a retraction configuration (i.e., one in which the instrument may be retracted into the entry guide) while changing associations between the input devices and instruments as necessary, and retracting each of the articulated instruments after its reconfiguration into the entry guide 2000. Therefore, it would be useful to provide a coupled control structure in which the entry guide controller 2273 is coupled to instrument controllers 2233, 2243, 2253, 2263 during "entry guide" mode so that the controllers 2233, 2243, 2253, 2263 automatically reconfigure and retract their respective articulated instruments upon receiving an indication to do so from the entry guide controller 2273. Reconfiguration and retraction of the articulated instruments may be performed sequentially (or concurrently when safe to do so) in this case either under the control of the Surgeon or automatically by the system while avoiding collisions among the instruments and with their environment.

Figure 16:
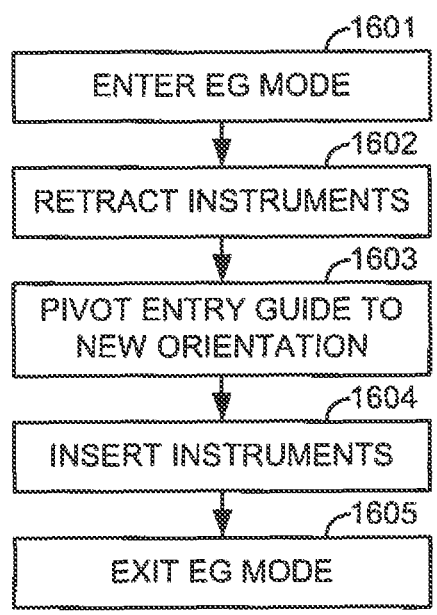
FIG. 16 illustrates a flow diagram of a method utilizing aspects of the present invention for re-orienting an entry guide with at least one articulated instrument disposed in it.
Figure 17:
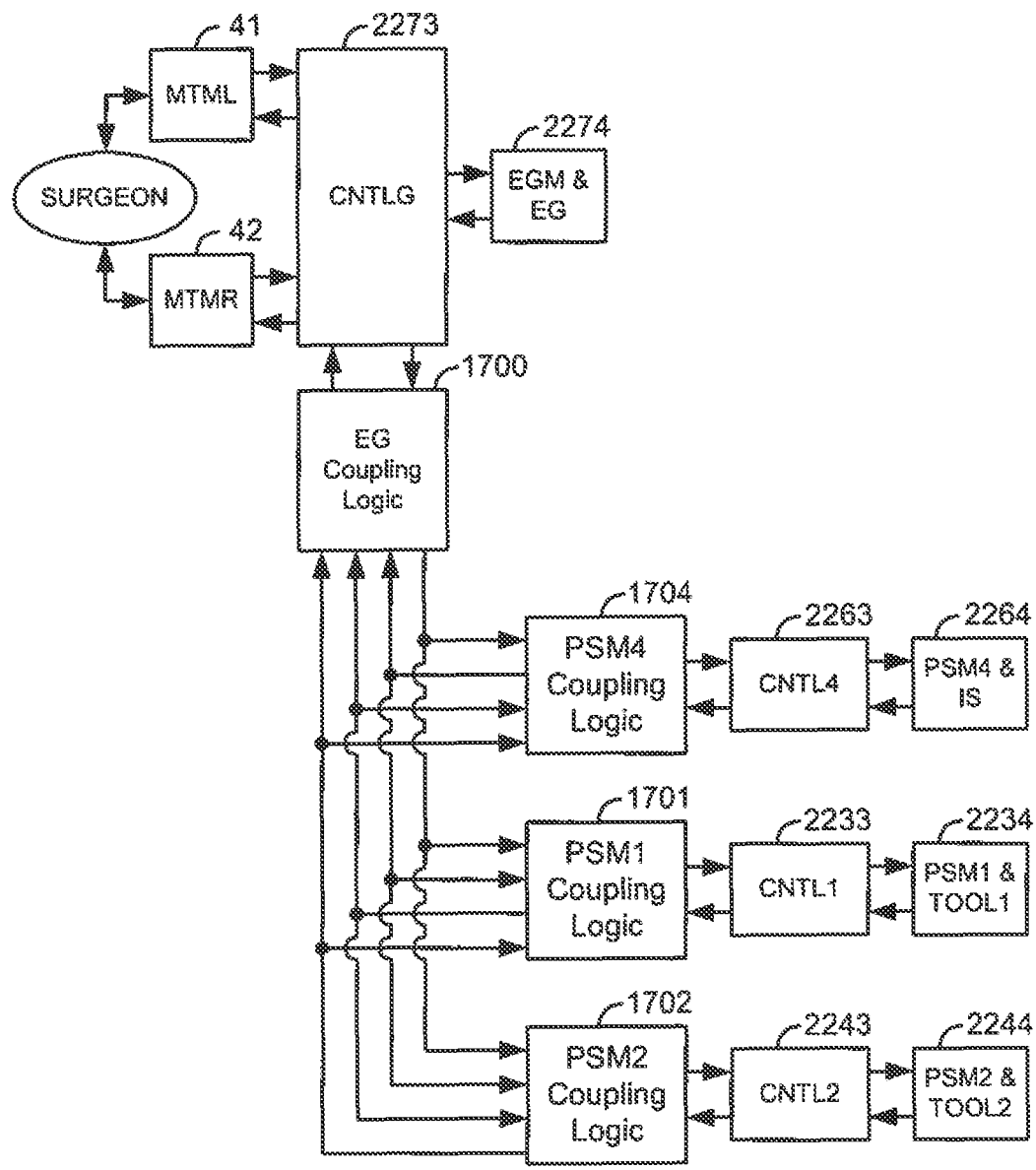
FIG. 17 illustrates a block diagram of components of a medical robotic system in an entry guide mode with coupled control of articulated instruments utilizing aspects of the present invention.

An example of such a coupled control structure is now described, wherein FIG. 16 illustrates a flow diagram including a method for re-orienting an entry guide having a plurality of extendable articulated instruments disposed within it and FIG. 17 illustrates a coupled control structure which includes one or more coupling logic blocks for implementing aspects of the method of FIG. 16.

Figure 18A:
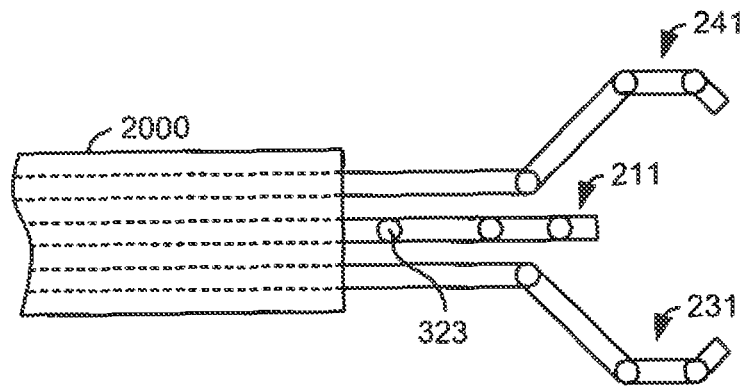
FIGS. 18A-18C illustrate top views of an entry guide in various stages of retracting articulated instruments into the entry guide in a medical robotic system utilizing aspects of the present invention.
Figure 18B:
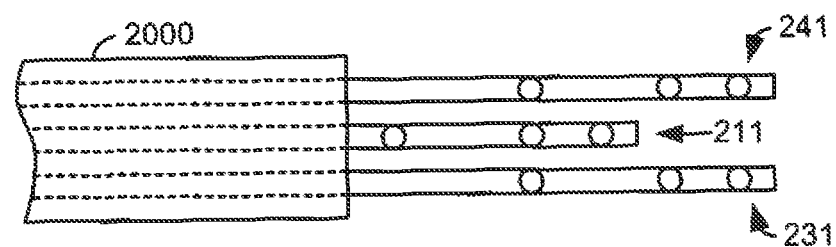
Figure 18C:
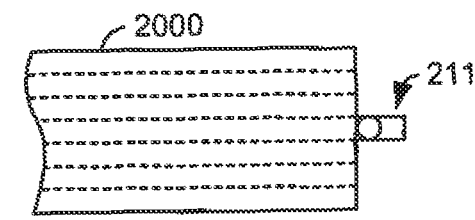

Referring to FIG. 16, in block 1601, the method receives an indication that the "entry guide" mode has been entered, as described, for example, in reference to FIG. 13. In block 1602, the method, in response to operator commands to do so, concurrently retracts all articulated instruments extending out of the distal end of the entry guide back into the entry guide either completely or at least to a point where they cannot harm the patient anatomy while the entry guide is being pivoted about the Remote Center (RC) pivot point. FIGS. 18A-18C serve to illustrate general aspects of the retraction performed in block 1602.

In FIG. 18A, a top view of the entry guide 2000 is shown with articulated instruments 231, 241, 211 extending out of its distal end such as shown in the perspective view of FIG. 7. In FIG. 18B, the articulated instruments 231, 241, 211 are shown in their retraction configurations wherein their links line up so as to be retractable into a corresponding lumen or space in the entry guide 2000. In FIG. 18C, the articulated tool instruments 231, 241 are shown fully retracted into the entry guide 2000 while the articulated camera instrument 211 is shown only partially retracted (or alternatively retracted so as to be just inside the entry guide) so that it may still capture a view out of the distal end while not risking harm to the patient anatomy when the entry guide 2000 is being pivoted about the RC pivot point. Alternatively, the articulated instruments 231, 241, 211 may not be fully retracted into the entry guide 2000, but only enough so that none of them may harm (or be placed in a position so as to cause unintended harm to) any patient anatomy when the entry guide 2000 is subsequently pivoted about the Remote Center (RC) to re-orient the entry guide 2000. Note that in this case, the articulated instruments 231, 241, 211 may be allowed to touch patient anatomy as long as the touching does not result in harming the patient anatomy.

Although the sequence shown in FIGS. 18A-18C suggests that the reconfiguration occurs before retraction starts, in practicing the invention, the sequence of retraction and reconfiguration of the plurality of articulated instruments may be performed concurrently or in a different order depending upon certain conditions and the method employed.

As first method of the retraction and reconfiguration sequence, if the most proximal joint of the plurality of articulated instruments (e.g. joint 323 of the articulated camera instrument 211 in FIG. 18A) is at a minimum distance away from the distal end of the entry guide 2000, then retraction may be allowed to occur concurrently with reconfiguration with a straightening velocity that is proportional to the retraction velocity (subject to maximum velocity limits). During reconfiguration and retraction, collisions between the reconfiguring and/or retracting instruments should be predicted by the system and avoided, as well as avoiding harm to the patient anatomy. The velocity with which the articulated instruments may be retracted and/or reconfigured is preferably a function of how hard the Surgeon is pushing against any haptic feedback being provided on the controlling input device during the retraction and/or reconfiguration. If the most proximal joint (that is not in the entry guide 2000 at the time) of the plurality of articulated instruments reaches the distal end of the entry guide 2000 before its articulated instrument has been fully reconfigured to its retraction configuration, then further retraction of the plurality of articulated instruments is prevented by the system until reconfiguration of the most proximal joint's articulated instrument into its retraction configuration has completed. This requirement is to avoid damage to the articulated instrument and/or entry guide 2000. In this case, the velocity for reconfiguration may still be a function of how hard the Surgeon is pushing against any haptic force being provided on the controlling input device, but possibly with a different gain. The minimum distance from the distal end of the entry guide 2000 at which concurrent retraction and reconfiguration may occur may be determined by consideration of several factors. One factor is the velocity at which in tandem movement of the articulated instruments is being commanded (e.g., the faster the commanded retraction movement, the larger the minimum distance; and the faster the reconfiguration movement, the smaller the minimum distance). Another factor is the initial configurations of the articulated instruments. For example, the closer the initial configurations of the plurality of articulated instruments are to their retraction configurations, the shorter the minimum distance, and vice versa. Also, since it is undesirable for the distal ends of the articulated instruments to extend forward beyond their initial positions during reconfiguration, because doing so may inadvertently harm the patient anatomy, compensation for such extension is required in the retraction direction. Therefore, the amount of such extension compensation is still another factor in determining the minimum distance.

As another and simpler method of the retraction and reconfiguration sequence, retraction may occur before reconfiguration. For example, the plurality of articulated instruments may be retracted in tandem until a most proximal joint (not already in the entry guide) of one of the articulated instruments reaches the distal end of the entry guide 2000, whereupon further retraction is prohibited by the system and reconfiguration of the articulated instrument into its retraction configuration is initiated. Once reconfiguration for that articulation instrument has completed, then the plurality of articulated instruments may be retracted in tandem again until a most proximal joint (not already in the entry guide) of one of the articulated instruments reaches the distal end of the entry guide 2000, whereupon further retraction is once again prohibited by the system and reconfiguration of that articulated instrument into its retraction configuration is initiated if necessary. The above described sequence would then continue until all of the plurality of articulated instruments has been thus reconfigured and retracted into the entry guide 2000.

Referring back to FIG. 16, in block 1603, the method, in response to operator commands to do so, pivots the entry guide 2000 about the RC pivot point to a new orientation. After completing the re-orientation of the entry guide 2000, in block 1604, the articulated instruments 231, 241, 211 may then be re-inserted in response to operator commands to do so, and in block 1605, the operator may exit the "entry guide" mode and enter "tool following" mode so that the operator (e.g., Surgeon) may perform or continue to perform a medical procedure on the patient with the re-positioned entry guide 2000 and articulated instruments 231, 241, 211.

Figure 19:
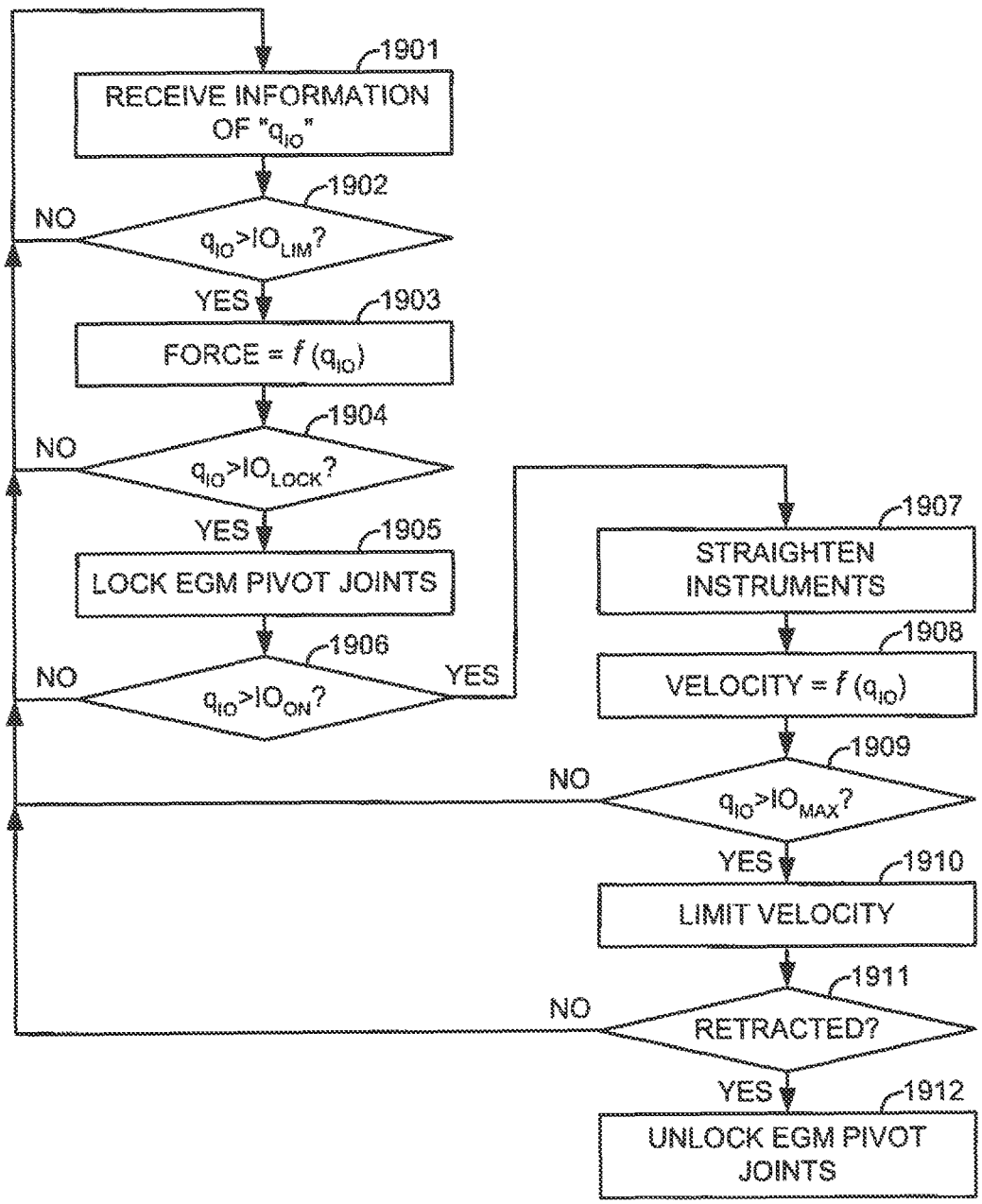
FIG. 19 illustrates a flow diagram of a method utilizing aspects of the present invention for moving a plurality of articulated instruments in tandem back towards an entry guide.

FIG. 19 illustrates, as an example, a flow diagram of a method for moving a plurality of articulated instruments in tandem back towards an entry guide, which method may be implemented by the coupled control structure of FIG. 17 and used to perform the articulated instrument retractions in block 1602 of FIG. 16.

In block 1901, the method receives information of a commanded change in the position ($q_{IO}$) of the entry guide 2000 in a direction parallel to the entry guide's insertion axis X'. The commanded position change in this case is relative to the RC point, which serves as an initial position from which the change in position is determined. In one embodiment, the commanded position change ($q_{IO}$) may be made by the Surgeon commanding the entry guide 2000 to move along its insertion axis X' when the system is in "entry guide" mode. In this case, however, instead of moving the entry guide 2000 along its insertion axis X', all articulated instruments extending out of the distal end of the entry guide 2000 are to be retracted back according to the commanded position change ($q_{IO}$).

Figure 20:
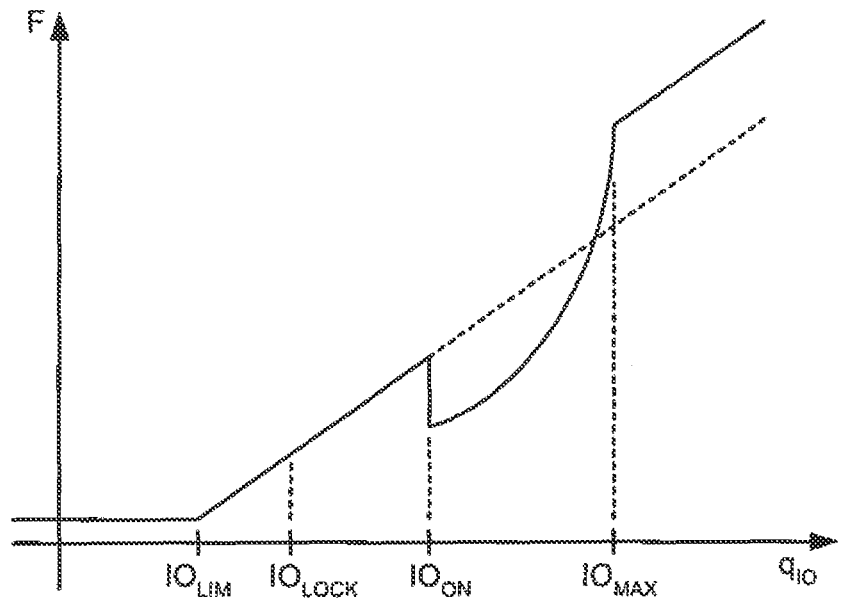
FIG. 20 illustrates a force versus commanded position change relationship usable in a method utilizing aspects of the present invention for moving at least one articulated instrument back towards an entry guide.

In block 1902, the method makes a determination whether the commanded position change ($q_{IO}$) is greater than a limit distance ($IO_{LIM}$). If the determination is NO, then the method loops back to block 1901 to receive information of another commanded position change ($q_{IO}$). On the other hand, if the determination in block 1902 is YES, then in block 1903, the method causes a haptic force to be applied against a control mechanism, which the operator uses to generate the commanded position change ($q_{IO}$), in a manner so as to progressively increase in force as the position change commands along the insertion axis X' generated by the operator manipulating the control mechanism progressively exceed the limit distance ($IO_{LIM}$), as depicted, for example, in the force versus commanded position change ($q_{IO}$) function of FIG. 20. The control mechanism in this case may include one or both of the input devices 41, 42 of the Surgeon console 2102.

In block 1904, the method makes a determination whether the commanded position change ($q_{IO}$) is greater than a locking distance ($IO_{LOCK}$), wherein the locking distance is greater than the limit distance. If the determination is NO, then the method loops back to block 1901 to receive information of another commanded position change ($q_{IO}$). On the other hand, if the determination in block 1904 is YES, then in block 1905, the method causes pivot joints of the entry guide manipulator (EGM) 2116 to be soft-locked in place using their respective joint controllers.

Figure 21:
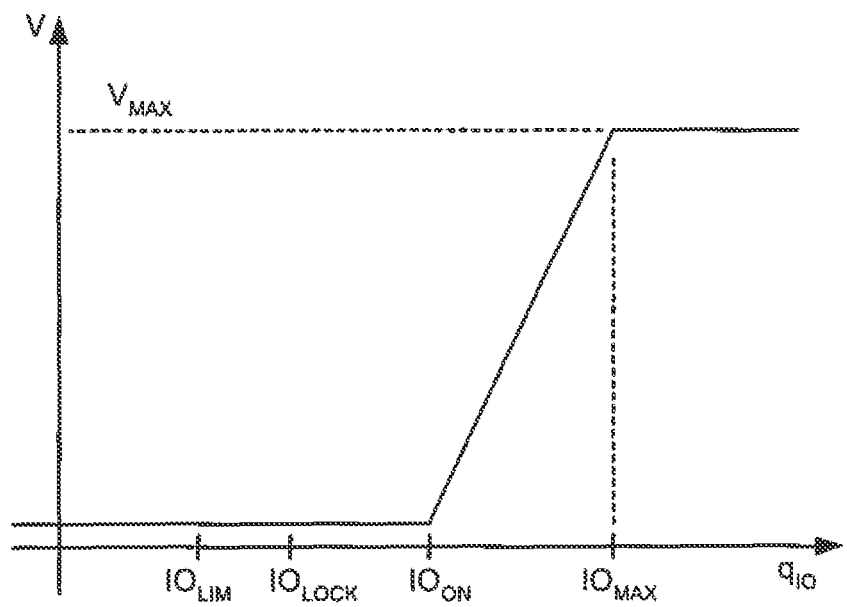
FIG. 21 illustrates a velocity versus commanded position change relationship usable in a method utilizing aspects of the present invention for moving at least one articulated instrument back towards an entry guide.

In block 1906, the method makes a determination whether the commanded position change ($q_{IO}$) is greater than a retraction-on distance ($IO_{ON}$), wherein the retraction-on distance is greater than the locking distance. If the determination is NO, then the method loops back to block 1901 to receive information of another commanded position change ($q_{IO}$). On the other hand, if the determination in block 1906 is YES, then in block 1907, the method causes the arms (e.g., the combination of joints and links) of the articulated instruments to be straightened so as to be in proper retraction configurations while concurrently in block 1908, the retractions of the articulated instruments are subjected to a progressively increasing velocity limit by the method as the commanded position change ($q_{IO}$) progressively exceeds the retraction-on distance, as depicted, for example, in the velocity versus commanded position change ($q_{IO}$) function of FIG. 21.

In block 1909, the method makes a determination whether the commanded position change ($q_{IO}$) is greater than a maximum distance ($IO_{MAX}$), wherein the maximum distance is greater than the retraction-on distance. If the determination is NO, then the method loops back to block 1901 to receive information of another commanded position change ($q_{IO}$). On the other hand, if the determination in block 1909 is YES, then in block 1910, the retractions of the articulated instruments are subject to a maximum velocity limit ($V_{MAX}$) as the commanded position changes progressively exceed the maximum distance, as depicted, for example, in the velocity versus commanded position change ($q_{IO}$) function of FIG. 21.

In block 1911, the method determines whether all articulated instruments previously extending out of the distal end of the entry guide 2000 are now in their retracted positions in the entry guide 2000. A retracted position in this case does not necessarily mean that the instrument is completely retracted into the entry guide 2000. As shown in FIG. 18C, for example, the articulated camera instrument 211 may still have its image capturing end exposed out of the entry guide 2000 so that it may get a better view of the surrounding area when the entry guide 2000 is being re-oriented by pivoting it about the RC point. This allows the Surgeon to view the portion of the patient anatomy where the entry guide 2000 is being re-oriented towards. Other articulated instruments may also be only partially retracted as long as their extended portions do not strike and harm the patient anatomy during the entry guide 2000 pivoting.

If the determination in block 1911 is NO, then the method loops back to block 1901 to receive information of another commanded position change ($q_{IO}$). On the other hand, if the determination in block 1911 is YES, then in block 1912, the method causes pivot joints of the entry guide manipulator (EGM) 2116 to no longer be soft-locked in place by their respective joint controllers. At this point, the entry guide 2000 may be re-oriented along with all articulated instruments disposed within it and the instruments may then be extended out of the entry guide 2000 so as to be positioned to perform or continue to perform a medical procedure on the patient.

Referring to FIG. 17, the methods described in reference to FIGS. 16 and 19 may be implemented in one or more of an EG coupling logic 1700, PSM1 coupling logic 1701, PSM2 coupling logic 1702, and PSM4 coupling logic 1704 for the example in which articulated instruments 2231, 2241, 2261 are disposed within the entry guide 2000. If more or less articulated instruments are extendable through the entry guide 2000, then the coupling structure of FIG. 17 may be modified accordingly. Although shown as separate components, the coupling logic 1700, 1701, 1702, 1704 may be structured as a single logic block by, for example, incorporating all logic into the EG coupling logic 1700, or it may be structured in a distributed processing fashion by, for example, eliminating the EG coupling logic 1700 and distributing the processing among the PSM1, PSM2, and PSM4 coupling logic 1701, 1702, 1704. Also, although shown as being separate from their respective controllers, each of the coupling logic blocks may be integrated into their respective controllers such as the EG coupling logic 1700 being integrated as part of the entry guide controller (CNTLG) 2273. Further, the processor 43 may implement all control and coupling logic shown in FIG. 17 using computer program code stored in a memory unit of the system 2100. To simplify the drawing, block 2274 represents the combination of the entry guide manipulator 2116 and entry guide 2000. Block 2264 represents the combination of the imaging system instrument manipulator 2262 and imaging system instrument 2261. Block 2234 represents the combination of the tool instrument manipulator 2232 and tool instrument 2231. Block 2244 represents the combination of the instrument manipulator 2242 and tool instrument 2241.

Figure 22:
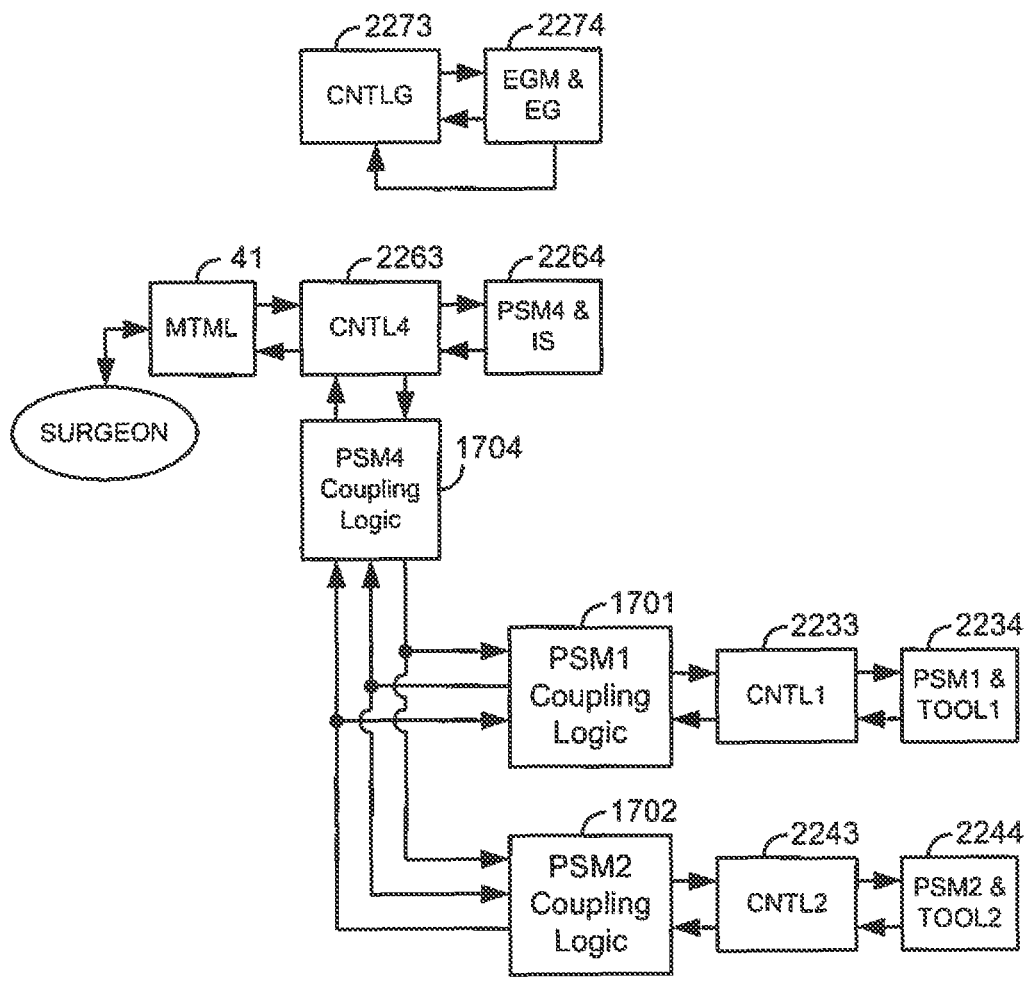
FIG. 22 illustrates a block diagram of components of a medical robotic system in a camera mode with coupled control of articulated instruments utilizing aspects of the present invention.
Figure 23:
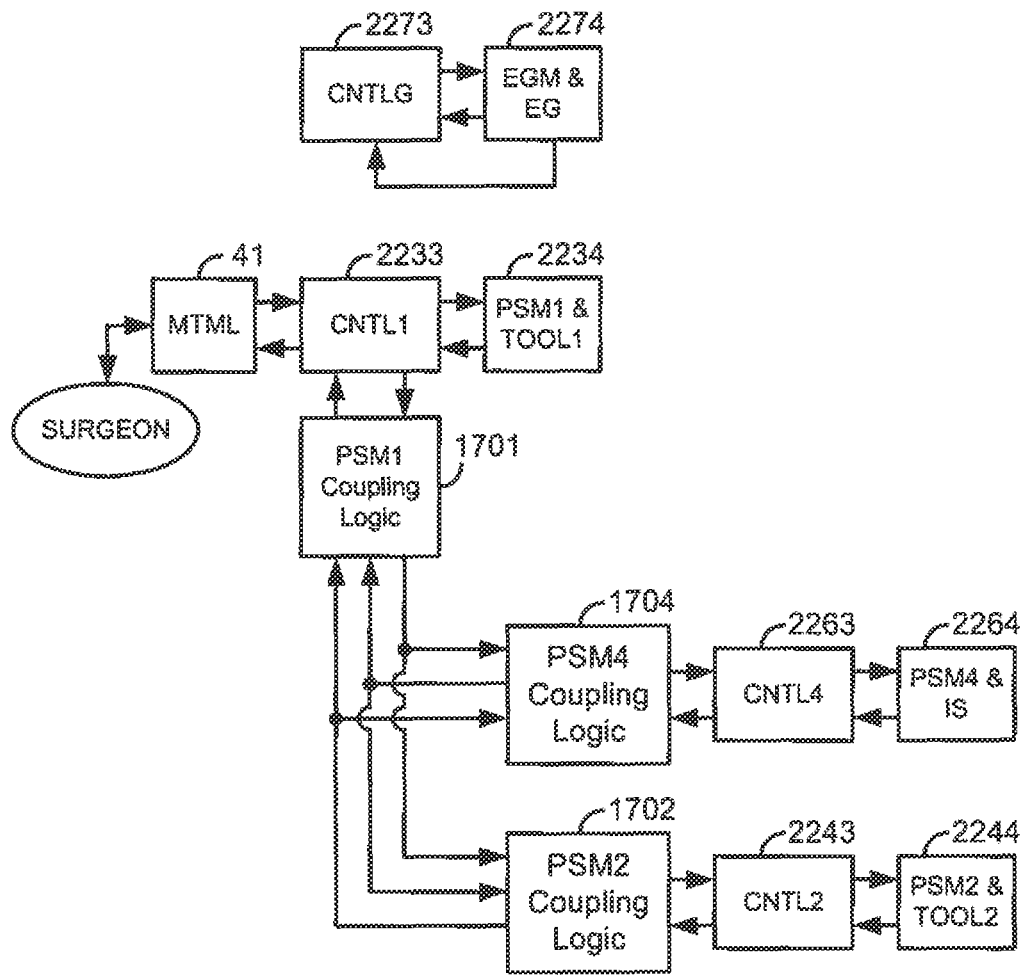
FIG. 23 illustrates a block diagram of components of a medical robotic system in an instrument following mode with coupled control of articulated instruments utilizing aspects of the present invention.
Figure 24:
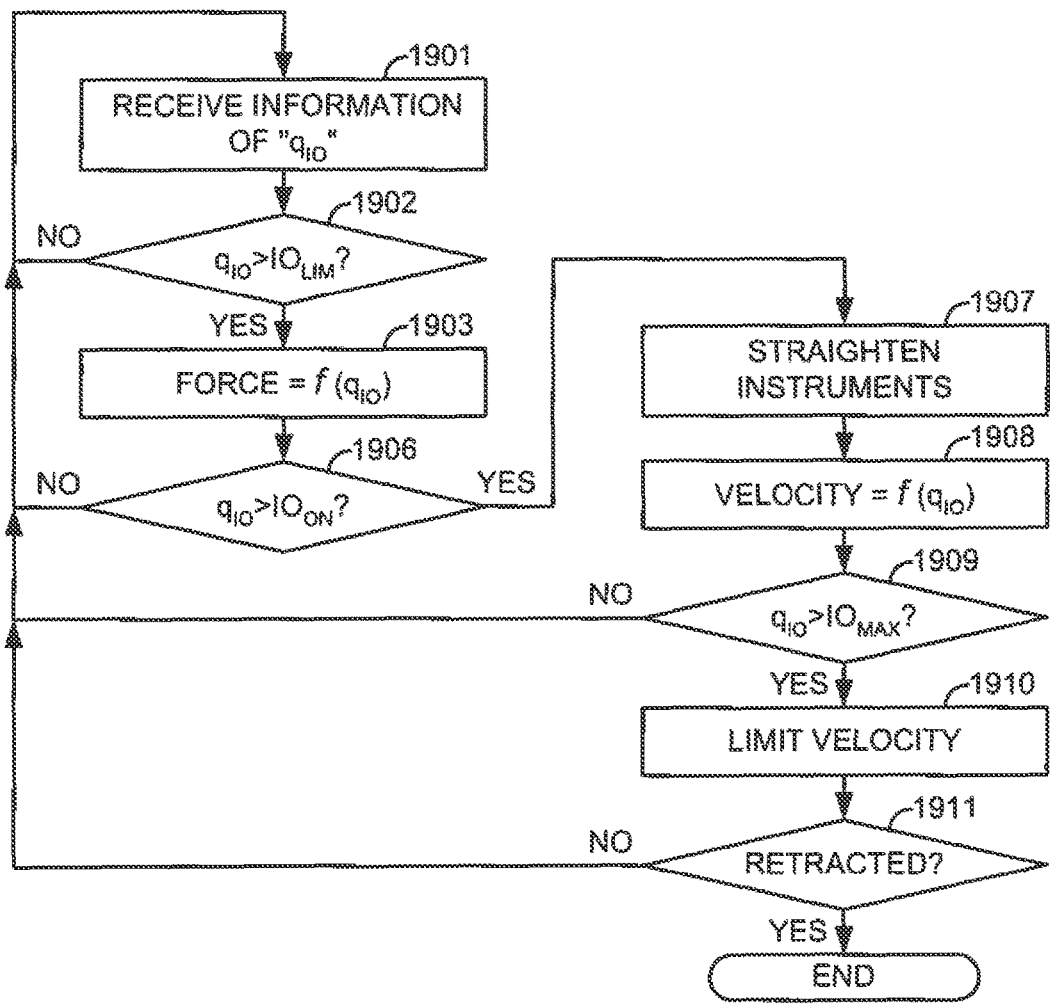
FIG. 24 illustrates a flow diagram of an alternative method utilizing aspects of the present invention for moving a plurality of articulated instruments in tandem back towards an entry guide.
Figure 25:
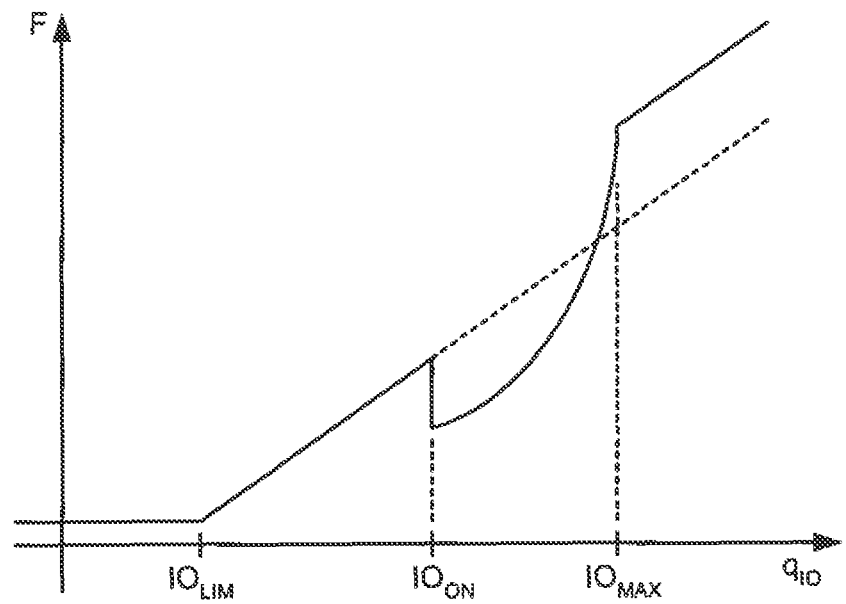
FIG. 25 illustrates a force versus commanded position change relationship usable in the alternative method utilizing aspects of the present invention for moving at least one articulated instrument back towards an entry guide.
Figure 26:
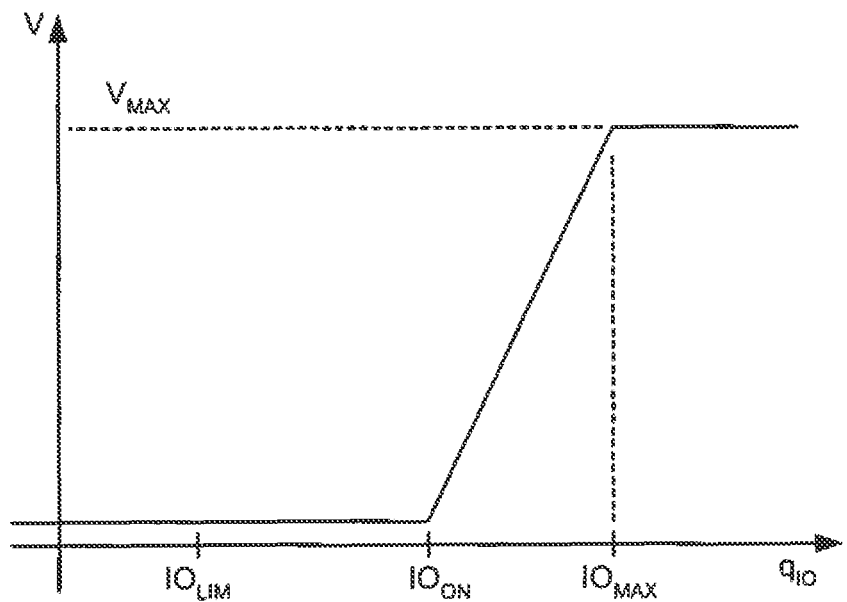
FIG. 26 illustrates a velocity versus commanded position change relationship usable in the alternative method utilizing aspects of the present invention for retracting at least one articulated instrument back towards an entry guide.

Although the moving of the articulated instruments 211, 231, 241 in tandem back towards the entry guide 2000 is described above in reference to re-orienting the entry guide 2000, it may also be useful to move a plurality of articulated instruments in tandem back towards the entry guide in other applications such as, for example, after the completion of a medical procedure. In these cases, rather than switching to the "entry guide" mode, the system may stay in an "imaging system" mode and make use of coupled control logic such as illustrated in FIG. 22 to move the articulated instruments 211, 231, 241 in tandem back towards the entry guide 2000. Likewise, the system may stay in a "tool following" mode and make use of coupled control logic such as illustrated in FIG. 23 to move the articulated instruments 211, 231, 241 in tandem back towards the entry guide 2000. In either case, the movement of the articulated instruments in tandem back towards the entry guide 2000 is performed in a similar manner as previously described with respect to FIGS. 19-21 with the exception that the pivot joints of the entry guide 2000 do not need to be locked. This is because under both "imaging system" mode and "tool following" mode, the entry guide 2000 is already locked in place (as illustrated, for example, in FIGS. 22, 23 by the "soft-locking" feedback from the entry guide and entry guide manipulator combination block 2274 to the entry guide controller 2273). Thus, FIGS. 24-26 illustrate a method for moving a plurality of articulated instruments (e.g., 211, 231, 241) in tandem back towards the entry guide 2000 that may be performed during "imaging system" and "tool following" modes, wherein FIG. 24 is performed substantially the same manner as described in reference to FIG. 19 with the exception that blocks 1904, 1905, 1912 related to locking the entry guide in place are deleted and FIGS. 25, 26 are respectively essentially the same as FIGS. 20, 21 with the exception that the point $IO_{LOCK}$ related to locking the entry guide in place has been deleted.

Although the various aspects of the present invention have been described with respect to a preferred embodiment, it will be understood that the invention is entitled to full protection within the full scope of the appended claims.

What is claimed is:

1. A method for moving an articulated instrument back towards an entry guide, out of which the articulated instrument extends, with automatic reconfiguration of the articulated instrument for retraction into the entry guide, the method comprising:
receiving, at a processor, information of a command, initiated from a control mechanism, to change the position of the articulated instrument in a direction parallel to a longitudinal axis of the entry guide;

determining, by the processor, whether the information of the command indicates the position of the articulated instrument is to be moved back towards the entry guide by a distance greater than a retraction-on distance in the direction parallel to the longitudinal axis of the entry guide relative to an initial position; and on the condition that the information of the command indicates the position of the articulated instrument is to be moved back towards the entry guide by the distance greater than the retraction-on distance from the initial position, automatically commanding, by the processor, the articulated instrument to be reconfigured towards a retraction configuration suitable for entering the entry guide while the position of the articulated instrument is being changed in response to the command initiated from the control mechanism.

2. The method of claim 1, further comprising:

on the condition that the information of the command indicates the distal end of the articulated instrument is to be moved back towards the entry guide by the distance greater than the retraction-on distance from the initial position, automatically commanding, by the processor, an abrupt change to a haptic force applied against the control mechanism.

3. The method of claim 1, further comprising:

receiving, at the processor, information of a sequence of commands, initiated from the control mechanism, to change the position of the articulated instrument in the direction parallel to the longitudinal axis of the entry guide;

determining, by the processor, whether the information of the sequence of commands from the control mechanism indicates the distal end of the articulated instrument is to be moved back towards the entry guide by distances which progressively exceed a limit distance from the initial position, wherein the limit distance is less than the retraction-on distance; and on the condition that the information of the sequence of commands from the control mechanism indicates the distal end of the articulated instrument is to be moved back towards the entry guide by distances which progressively exceed a limit distance from the initial position, automatically commanding, by the processor, a progressively increasing haptic force applied against the control mechanism in response to the sequence of commands from the control mechanism.

4. The method of claim 3, further comprising:

on the condition that the information of the command indicates the position of the articulated instrument is to be moved back towards the entry guide by the distance greater than the retraction-on distance from the initial position, automatically commanding, by the processor, movement of the articulated instrument to be subject to a progressively increasing velocity limit as the sequence of commands indicate the articulated instrument is to be moved back towards the entry guide by distances which progressively exceed the retraction-on distance from the initial position.

5. The method of claim 3, further comprising:

determining, by the processor, whether one command of the sequence of commands indicates the articulated instrument is to be moved back towards the entry guide by a distance that exceeds a maximum velocity distance from the initial position, wherein the maximum velocity distance is greater than the retraction-on distance; and on the condition that the information of the sequence of commands indicates the articulated instrument is to be moved back towards the entry guide by the distance that exceeds the maximum velocity distance from the initial position, automatically commanding, by the processor, the articulated instrument to be moved in a manner which is subject to a maximum velocity limit.

6. A robotic system comprising:

a control mechanism;

an entry guide;

an articulated instrument extending out of a distal end of the entry guide;

an instrument manipulator configured to manipulate the articulated instrument; and a processor programmed to:

receive information of a command, initiated from the control mechanism, to change a position of the articulated instrument in a direction parallel to a longitudinal axis of the entry guide;

determine whether the information of the command indicates the position of the articulated instrument is to be moved back towards the entry guide by a distance greater than a retraction-on distance in the direction parallel to the longitudinal axis of the entry guide relative to an initial position; and on the condition that the information of the command indicates the position of the articulated instrument is to be moved back towards the entry guide by the distance greater than the retraction-on distance from the initial position, automatically command the instrument manipulator to reconfigure the articulated instrument towards a retraction configuration suitable for entering the entry guide while the position of the articulated instrument is being changed in response to the command initiated from the control mechanism.

7. The system of claim 6, wherein the processor is programmed to:

cause an abrupt change to a haptic force being applied against the control mechanism upon the command initiated from the control mechanism indicating the articulated instrument is to be moved back towards the entry guide by the distance greater than the retraction-on distance from the initial position.

8. The system of claim 6, wherein the processor is programmed to:

cause a progressively increasing haptic force to be applied against the control mechanism in response to a sequence of commands from the control mechanism to move the articulated instrument back towards the entry guide by distances which progressively exceed a limit distance from the initial position, wherein the limit distance is less than the retraction-on distance, and wherein the progressively increasing haptic force, the sequence of commands, and the distances which progressively exceed a limit distance correspond.

9. The system of claim 8, wherein the processor is programmed to:

on the condition that the information of the command indicates the position of the articulated instrument is to be moved back towards the entry guide by the distance greater than the retraction-on distance from the initial position, automatically command the instrument manipulator to move the articulated instrument so as to be subject to a progressively increasing velocity limit as the sequence of commands correspondingly indicate the articulated instrument is to be moved back towards the entry guide by distances which progressively exceed the retraction-on distance from the initial position.

10. The system of claim 8, wherein the processor is programmed to:
   determine whether one of the sequence of commands indicates the articulated instrument is to be moved back towards the entry guide by a distance that exceeds a maximum velocity distance from the initial position, wherein the maximum velocity distance is greater than the retraction-on distance; and
   on the condition that the information of the sequence of commands indicates the articulated instrument is to be moved back towards the entry guide by the distance that exceeds the maximum velocity distance from the initial position, automatically command the instrument manipulator to move the articulated instrument in a manner which is subject to a maximum velocity limit.

* * * * *